(12) United States Patent
Harwood et al.

(10) Patent No.: US 11,759,594 B2
(45) Date of Patent: Sep. 19, 2023

(54) HME AND COMPACT BREATHING APPARATUS

(71) Applicant: Fisher & Paykel Healthcare Limited, Auckland (NZ)

(72) Inventors: Jonathan David Harwood, Auckland (NZ); Andrew John Partington, Auckland (NZ); Andrew Paul Maxwell Salmon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/589,530

(22) Filed: Oct. 1, 2019

(65) Prior Publication Data

US 2020/0164172 A1 May 28, 2020

Related U.S. Application Data

(63) Continuation of application No. 15/028,542, filed as application No. PCT/IB2014/065194 on Oct. 10, 2014, now Pat. No. 10,471,230.

(Continued)

(51) Int. Cl.
*A61M 16/10* (2006.01)
*A61M 16/00* (2006.01)
(Continued)

(52) U.S. Cl.
CPC .... *A61M 16/1045* (2013.01); *A61M 16/0066* (2013.01); *A61M 16/0875* (2013.01);
(Continued)

(58) Field of Classification Search
CPC .......... A61M 16/0066; A61M 16/0808; A61M 16/0875; A61M 16/1045; A61M 2205/02;
(Continued)

(56) References Cited

U.S. PATENT DOCUMENTS

| 4,090,513 A | 5/1978 | Togawa |
| 4,737,153 A | 4/1988 | Shimamura |

(Continued)

FOREIGN PATENT DOCUMENTS

| EP | 0588214 B1 | 12/1998 |
| EP | 2647401 A1 | 10/2013 |

(Continued)

OTHER PUBLICATIONS

International Search Report; PCT/IB2014/065194; dated Mar. 5, 2015; 9 pages.

*Primary Examiner* — Colin W Stuart
*Assistant Examiner* — Matthew D Ziegler
(74) *Attorney, Agent, or Firm* — Knobbe, Martens, Olson & Bear, LLP

(57) ABSTRACT

An adjustable heat and moisture exchanger (HME) for use with a breathing apparatus to humidify air comprising: an inlet for coupling to a source of air, and an outlet for delivering air to a patient and an air flow path between them, HME material in the flow path with two or more surfaces exposed to the air flow path to exchange humidity between patient air flow and an inlet air flow, at least one adjuster for adjusting the configuration of the HME material and/or the air flow to alter the air flow over the surfaces of the HME material to alter the exchange of humidity.

19 Claims, 30 Drawing Sheets

Related U.S. Application Data

(60) Provisional application No. 61/889,944, filed on Oct. 11, 2013, provisional application No. 61/906,307, filed on Nov. 19, 2013, provisional application No. 61/985,233, filed on Apr. 28, 2014.

(51) Int. Cl.
*A61M 16/08* (2006.01)
*A62B 23/02* (2006.01)

(52) U.S. Cl.
CPC ..... *A61M 16/0808* (2013.01); *A61M 2205/02* (2013.01); *A61M 2205/7536* (2013.01); *A62B 23/02* (2013.01)

(58) Field of Classification Search
CPC ........ A61M 2205/7536; A61M 16/209; A62B 23/02; A62B 9/02–027; A62B 18/10
USPC .................................................. 128/207.18
See application file for complete search history.

(56) References Cited

U.S. PATENT DOCUMENTS

| | | | |
|---|---|---|---|
| 4,771,770 A | 9/1988 | Artemenko et al. | |
| 5,007,421 A | 4/1991 | Stewart | |
| 5,394,867 A | 3/1995 | Swann | |
| 5,584,286 A | 12/1996 | Kippax | |
| 5,617,913 A | 4/1997 | DeGregoria | |
| 5,701,891 A | 12/1997 | Groenke | |
| 6,006,748 A * | 12/1999 | Hollis | A61M 16/06 128/205.24 |
| 6,330,883 B1 | 12/2001 | Berger | |
| 6,478,026 B1 * | 11/2002 | Wood | A61M 16/0666 128/207.13 |
| 6,550,476 B1 | 4/2003 | Ryder | |
| 6,745,766 B2 | 6/2004 | Fini | |
| 7,559,327 B2 * | 7/2009 | Hernandez | A61M 16/06 128/203.22 |
| 8,397,727 B2 * | 3/2013 | Ng | A61M 16/1065 128/206.21 |
| 9,155,857 B2 * | 10/2015 | Lalonde | A61M 16/204 |
| 9,289,568 B2 * | 3/2016 | Dhuper | A61M 16/127 |
| 9,717,870 B2 * | 8/2017 | Kwok | A61M 16/06 |
| 9,821,136 B2 * | 11/2017 | Nitta | A61M 16/202 |
| 10,029,058 B2 * | 7/2018 | Foote | A61M 16/202 |
| 10,589,042 B2 * | 3/2020 | Holley | A61M 16/1045 |
| 2004/0084046 A1 | 5/2004 | Halperin | |
| 2004/0123974 A1 | 7/2004 | Marler et al. | |
| 2006/0219243 A1 | 10/2006 | Walstrom | |
| 2007/0095350 A1 | 5/2007 | Darkin | |
| 2008/0099013 A1 | 5/2008 | Graham | |
| 2008/0283053 A1 | 11/2008 | Zucchi | |
| 2009/0266364 A1 | 10/2009 | Nysaether | |
| 2009/0301476 A1 | 12/2009 | Korneff | |
| 2010/0059055 A1 | 3/2010 | Brungart | |
| 2010/0263669 A1 * | 10/2010 | Bowsher | A61M 16/208 128/204.29 |
| 2011/0082380 A1 | 4/2011 | Breen | |
| 2011/0226250 A1 | 9/2011 | LaBollita et al. | |
| 2012/0097156 A1 * | 4/2012 | Bowman | A61M 16/06 128/201.13 |
| 2013/0068219 A1 | 3/2013 | Collazao | |
| 2014/0305431 A1 | 10/2014 | Holley | |
| 2015/0053368 A1 | 2/2015 | Umehara et al. | |

FOREIGN PATENT DOCUMENTS

| | | |
|---|---|---|
| EP | 2705949 A1 | 3/2014 |
| WO | WO 2008/011683 | 1/2008 |
| WO | WO 2009/149290 | 12/2009 |
| WO | WO 2011/022779 | 3/2011 |
| WO | WO 2012/174602 | 12/2012 |

* cited by examiner

HME AND COMPACT BREATHING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The presently disclosed subject matter relates to providing adjustable humidification using heat and moisture exchangers (HME) as part of breathing assistance using a breathing assistance apparatus. The present invention also relates to breathing apparatus that are compact and can be maneuvered to convenient locations. Such breathing apparatus could be (although are not limited to) continuous positive airway pressure (CPAP), bilevel, auto titration apparatus or non-invasive ventilators or any other breathing apparatus that provides pressure and/or airflow to a patient. Such apparatus can use adjustable humidification.

BACKGROUND

Breathing apparatus are used to provide breathing assistance to patients. Examples of such breathing apparatus are CPAP (continuous positive airway pressure), bi-level and/or autotitration PAP (positive airway pressure) apparatus that provide pressure support to a patient for treating obstructive sleep apnea or other breathing disorders. Other examples of such breathing apparatus are ventilators (such as non-invasive ventilation—NIV) that provide assisted breathing or flow therapy.

Often as part of therapy and/or for comfort it is desirable to humidify the air provided to the patient by the breathing apparatus.

SUMMARY OF INVENTION

It is an object of the presently disclosed subject matter to provide an apparatus and/or method for adjustable humidification alone or as part of a breathing apparatus.

It is an alternative object of the presently disclosed subject matter to provide a breathing apparatus that is portable and/or can be positioned in more convenient locations during used.

In one aspect the presently disclosed subject matter invention may be said to comprise an adjustable HME for use with a breathing apparatus to humidify air comprising:
  an inlet for coupling to a source of air, and an outlet for delivering air to a patient and an air flow path between them,
  HME material in the flow path with two or more surfaces exposed to the air flow path to exchange humidity between patient air flow and an inlet air flow,
  at least one adjuster for adjusting the configuration of the HME material and/or the air flow to alter the air flow over the surfaces of the HME material to alter the exchange of humidity.

Preferably the HME material is spiral wound on a spindle and the adjuster manipulates the spindle to tighten or loosen the spiral of HME material and/or adjust the diameter of the spiral.

Preferably the adjuster comprises adjustable apertures for altering the inlet airflow and/or patient air flow over surfaces of the HME material to alter the exchange of moisture and/or humidity.

Preferably the adjustable apertures comprise two sets of apertures and corresponding cover(s), a first set being arranged on the outlet side of the flow path and a second set being arranged on the inlet side of the flow path.

Preferably the cover is a slidable cover that is moveable relative to the first set and second set apertures to cover none, part or all of the apertures of each set, wherein covering some or all of the first set of apertures reduces patient air flow to atmosphere through the first set to increase patient air flow through the HME material to increase the exchange of humidity.

Preferably the cover is a rotatable cover that is moveable relative to the first set and second of set apertures to cover none, part or all of the apertures of each set, wherein covering some or all of the first set of apertures reduces patient air flow to atmosphere through the first set to increase patient air flow through the HME material to increase the exchange of humidity.

Preferably the cover is a rotatable cover that is moveable relative to the first set of apertures to cover none, part or all of the apertures of each set, wherein covering some or all of the first set of apertures diverts some or all of the patient air flow past the HME material through the second set of apertures to decrease patient air flow through the HME material to decrease the exchange of humidity.

Preferably the HME material comprises a sheet with raised portions.

Preferably the HME material is coiled, layered and/or stack to form air paths.

Preferably the HME material is metal or polymer.

Preferably the HME further comprises a valve in the air flow wherein the adjuster manipulates the valve to control the volume of air flow over the HME material.

Preferably the HME material provides a condensation and absorption surface further comprising a valve in the air flow and the adjuster manipulates the valve to control the volume of air flow.

Preferably the HME further comprises a HME chamber with a tubular extension with an aperture coaxially rotatably coupled to a patient duct with an aperture, wherein the apertures form the valve and the adjuster manipulates the valve by rotating the tubular extension relative to the patient duct to alter alignment of the apertures.

In another aspect the presently disclosed subject matter comprises an adjustable HME for use with a breathing apparatus to humidify air comprising:
  an inlet for coupling to a source of air, and an outlet for delivering air to a patient and an air flow path between them,
  HME material in the flow path with two or more surfaces exposed to the air flow path to exchange humidity between a patient airflow and an inlet air flow, wherein the HME material is spiral wound on a spindle
  at least one adjuster for rotating the spindle to loosen or tighten the spiral and/or increase or reduce the diameter of the spiral to alter the patient and inlet air flows exposed to the surfaces of the HME material to alter the exchange of humidity.

In another aspect the present invention may be said to consist in an adjustable HME for use with a breathing apparatus to humidify air comprising:

an inlet duct for coupling to a source of air, and an outlet duct for delivering air to a patient and an air flow path between them, an HME chamber with HME material in the flow path with two or more surfaces exposed to the air flow path to exchange humidity between a patient airflow and an inlet air flow, the HME chamber rotationally coupled to the outlet duct, the HME chamber having an aperture rotatable relative to an aperture in a side wall of the outlet duct for passage of the patient air flow, at least one adjuster for rotating the HME chamber relative to the patient duct to adjust the combined aperture size to control the patient air flow over the HME surface.

In another aspect the present invention relates to a breathing system or breathing apparatus comprising an adjustable HME that is directly or indirectly between an outlet and the patient, according to any paragraph above.

Preferably the adjustable HME further comprises bias flow holes at a distal end of the HME with respect to the patient after the HME material so exhaled patient airflow laden with humidity passes over the HME material prior to passing through the bias flow holes to ambient.

In another aspect the present invention may be said to consist in an HME comprising metal mesh or metal covered mesh.

Preferably the metal is copper or aluminium.

In another aspect the present invention may be said to consist in an HME comprising a molecular sieve.

Preferably the HME comprises zeolite granules or synthetic zeolite granules.

In another aspect the present invention may be said to consist in metal mesh (such as aluminium or copper) or metal covered plastic mesh for use in an HME.

In another aspect the present invention may be said to consist in zeolite granules or synthetic zeolite granules for use in an HME.

Preferably the HME material is aluminium mesh, Zeolite granules, or metal covered mesh.

In another aspect the present invention may be said to consist in an HME with HME material comprising a water chamber surrounding and in fluid communication with the HME material.

In another aspect the present invention may be said to consist in a compact breathing apparatus for providing flow or pressure to a patient, comprising: a housing with an inlet for receiving air and an outlet for providing airflow to a patient, a blower in the housing, the blower comprising an impeller coupled to a motor, wherein upon operation the blower rotates the impeller to draw air from the inlet and pass it to the outlet, wherein the breathing apparatus is sufficiently compact to enable portability and placement of the breathing apparatus in a range of convenient locations.

Preferably the apparatus further comprises a flexible air inlet tube with an air inlet and an outlet coupled to the housing inlet wherein the flexible air inlet tube can be manipulated to position the air inlet away from occlusions when the compact breathing apparatus is placed in a convenient location.

Preferably the flexible air inlet tube is formed from a malleable material to enable manipulation of the tube into a range of geometric configurations to position the air inlet away from occlusions when the compact breathing apparatus is placed in a convenient location.

Preferably the flexible air inlet tube has reinforcing to enable manipulation of the flexible air inlet tube into a range of geometric configurations to position the air inlet away from occlusions when the compact breathing apparatus is placed in a convenient location.

Preferably the reinforcing is a malleable elongated insert (e.g. flexible wire) that can be positioned and retained in a range of geometric configurations to manipulate and hold the flexible air inlet tube into the range of geometric configurations.

Preferably the flexible air inlet tube is made from silicon rubber and/or has an internal diameter to wall section ratio of 3:1 (or anywhere from 3:1 to 6:1) to prevent occlusion of the flexible air inlet tube upon manipulation or external force.

Preferably the apparatus further comprises an HME (optionally adjustable) coupled directly or indirectly to the housing outlet to humidify air flow provided to the patient.

Preferably the apparatus further comprises a patient conduit and patient interface, wherein the HME and patient conduit are coupled between the housing outlet and the patient interface.

Preferably the patient conduit comprises exhaust vents to enable washout of $CO_2$ from patient expiration.

Preferably the exhaust vents are placed in a connector between the patient conduit on the patient interface, and the HME has exhaust vents, wherein upon connection of the HME between the patient conduit and the patient interface, the exhaust vents on the patient conduit are occluded.

Preferably the HME comprises a flexible hose for coupling to the patient interface, wherein the flexible hose has a 15 mm internal diameter (or anywhere between 10-20 mm) and/or is 50 to 100 mm long.

Preferably there are no external configuration controls accessible for user manipulation, and optionally further comprising a wireless interface for wireless configuration and/or interrogation of the apparatus using a remote device.

Preferably the patient conduit is approximately 800 to 1000 mm long and/or 15 mm internal diameter (or anywhere between 10-20 mm).

Preferably the housing comprises two abutting halves with a flexible outer cover over the abutment, and optionally the housing is an extended oval shape with dimensions of 110×120×45 mm, or anywhere between 80-120 mm×80-120 mm×40-60 mm.

Preferably the flexible air inlet tube terminates in a replaceable filter element.

Preferably the filter element has a housing with openings at the end and along the side, and optionally is in the shape of a cone.

Preferably the flow generator housing halves are internally lined with a sound deadening material.

In another aspect the present invention may be said to consist in an adjustable HME for use with a breathing apparatus to humidify air comprising: an inlet for coupling to a source of air, and an outlet for delivering air to a patient and an air flow path between them, HME material in the flow path, and exposed to the air flow path to exchange heat and moisture and/or humidity between patient air flow and an inlet air flow, adjustable apertures for altering the inlet airflow and/or patient air flow over surfaces of the HME material to alter the exchange of moisture and/or humidity.

Preferably the adjustable apertures comprise one or more apertures and one or more corresponding covers moveable relative to the apertures to cover none, part or all of the apertures to control inlet air flow and patient air flow through the apertures.

Preferably the adjustable apertures comprise two sets of apertures and corresponding cover(s), a first set being arranged on the outlet side of the flow path and a second set being arranged on the inlet side of the flow path.

Preferably the HME further comprises a housing around the HME material and air flow path, wherein the adjustable apertures are in the housing to control patient air flow and/or inlet air flow to atmosphere.

Preferably the cover is a slidable cover that is moveable relative to the first set and second set apertures to cover none, part or all of the apertures of each set, wherein covering some or all of the first set of apertures reduces patient air flow to atmosphere through the first set to increase patient air flow through the HME material to increase the exchange of humidity.

Preferably the cover is a rotatable cover that is moveable relative to the first set and second of set apertures to cover none, part or all of the apertures of each set, wherein covering some or all of the first set of apertures reduces patient air flow to atmosphere through the first set to increase patient air flow through the HME material to increase the exchange of humidity.

Preferably the cover is a rotatable cover that is moveable relative to the first set of apertures to cover none, part or all of the apertures of each set, wherein covering some or all of the first set of apertures diverts some or all of the patient air flow past the HME material through second set of apertures to decrease patient air flow through the HME material to decrease the exchange of humidity.

Preferably the HME material is sheet material with raised portions and is one or more of:
 a coiled or layered or stacked metal mesh or metal covered mesh; or
 a coiled or layered or stacked polymer mesh.

In another aspect the present invention may be said to consist in an HME according to any of the paragraphs above, wherein the HME is incorporated into an interface.

In another aspect the present invention may be said to consist in an HME according to any of the paragraphs above, wherein the HME is a modular HME configure to be connected between a mask shell or housing and a mask frame.

In another aspect the present invention may be said to consist in an HME according to any of the paragraphs above An HME for use with a breathing apparatus to humidify air comprising: an inlet for coupling to a source of air, and an outlet for delivering air to a patient and an air flow path between them, HME material in the flow path, and exposed to the air flow path to exchange heat and moisture and/or humidity between patient air flow and an inlet air flow, wherein the HME material is sheet material with raised portions and is coiled, layered and/or stacked.

Preferably the HME material is metal mesh or metal covered mesh or polymer mesh.

Preferably the material is expanded material to form the raised portions.

Preferably the material is woven material.

Preferably the HME material is pressed/welded material.

In another aspect the present invention may be said to consist in an HME material comprising a sheet with raised portions.

Preferably the material is coiled, layered and/or stack to form air paths.

Preferably the material is expanded material to form raised portions.

Preferably the material is woven material.

Preferably the material is pressed/welded material.

Preferably the material is metal or polymer.

In another aspect the present invention may be said to consist in an HME comprising metal mesh or metal covered mesh, which is optionally non-corrosive.

Preferably the metal is copper or aluminium.

In another aspect the present invention may be said to consist in an HME comprising a polymer, such as nylon or polypropylene.

In another aspect the present invention may be said to consist in a modular HME configured to retrofit to a patient interface.

Preferably the HME comprises a housing configured to couple between a mask shell and mask frame of a patient interface.

Preferably the HME comprises HME material according as described in any paragraph above.

In another aspect the present invention may be said to consist in a modular HME that is an adjustable HME according to any paragraph above.

In another aspect the present invention may be said to consist in a bias flow hole cover for a patient interface, optionally adjustable to cover none, some or all of the bias flow holes of a patient interface.

In another aspect the present invention may be said to consist in a compact breathing apparatus for providing flow or pressure to a patient, comprising: a housing with an inlet for receiving air and an outlet for providing airflow to a patient, a blower in the housing, the blower comprising an impeller coupled to a motor, wherein upon operation the blower rotates the impeller to draw air from the inlet and pass it to the outlet, wherein the breathing apparatus is sufficiently compact to enable portability and placement of the breathing apparatus in a range of convenient locations.

Preferably the breathing apparatus further comprises a flexible air inlet tube with an air inlet and an outlet coupled to the housing inlet wherein the flexible air inlet tube can be manipulated to position the air inlet away from occlusions when the compact breathing apparatus is placed in a convenient location.

Preferably the flexible air inlet tube is formed from a malleable material to enable manipulation of the tube into a range of geometric configurations to position the air inlet away from occlusions when the compact breathing apparatus is placed in a convenient location.

Preferably the flexible air inlet tube has reinforcing to enable manipulation of the flexible air inlet tube into a range of geometric configurations to position the air inlet away from occlusions when the compact breathing apparatus is placed in a convenient location.

Preferably the reinforcing is a malleable elongated insert (e.g. flexible wire) that can be positioned and retained in a range of geometric configurations to manipulate and hold the flexible air inlet tube into the range of geometric configurations.

Preferably the flexible air inlet tube is made from silicon rubber and/or has an internal diameter to wall section ratio of 3:1 (or anywhere from 3:1 to 6:1) to prevent occlusion of the flexible air inlet tube upon manipulation or external force.

Preferably the breathing apparatus further comprises an HME (optionally adjustable) coupled directly or indirectly to the housing outlet to humidify air flow provided to the patient.

Preferably the patient conduit is approximately 800 to 1000 mm long and/or 15 mm internal diameter (or anywhere between 10-20 mm).

Preferably the housing comprises two abutting halves with a flexible outer cover over the abutment, and optionally the housing is an extended oval shape with dimensions of 110×120×45 mm, or anywhere between 80-120 mm×80-120 mm×40-60 mm.

In another aspect the present invention may be said to consist in a compact breathing apparatus for providing flow or pressure to a patient, comprising: a housing with an inlet for receiving air and an outlet for providing airflow to a patient, a blower in the housing, the blower comprising an impeller coupled to a motor, wherein upon operation the blower rotates the impeller to draw air from the inlet and pass it to the outlet, and a flexible air inlet tube with an air inlet and an outlet coupled to the housing inlet wherein the flexible air inlet tube can be manipulated to position the air inlet away from occlusions when the compact breathing apparatus is placed in a convenient location.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The term "comprising" as used in this specification means "consisting at least in part of". When Interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Where specific integers are mentioned herein which have known equivalents in the art to which this invention relates, such known equivalents are deemed to be incorporated herein as if individually set forth.

The Invention consists in the foregoing and also envisages constructions of which the following gives examples only.

BRIEF DESCRIPTION OF DRAWINGS

Preferred embodiments of the drawings will be described with reference to the following drawings, of which.

DETAILED DESCRIPTION OF PREFERRED EMBODIMENTS

The presently disclosed subject matter relates to an adjustable HME, and a breathing apparatus comprising or utilising an adjustable HME for providing humidified air to a patient.

The presently disclosed subject matter relates also to an HME material comprising mesh material with raised portions that are stacked, layered or coiled to form air paths.

The presently disclosed subject matter relates also to a breathing apparatus that is portable and/or can be positioned in more convenient locations during used.

Breathing Apparatus with HME

Figure 1:
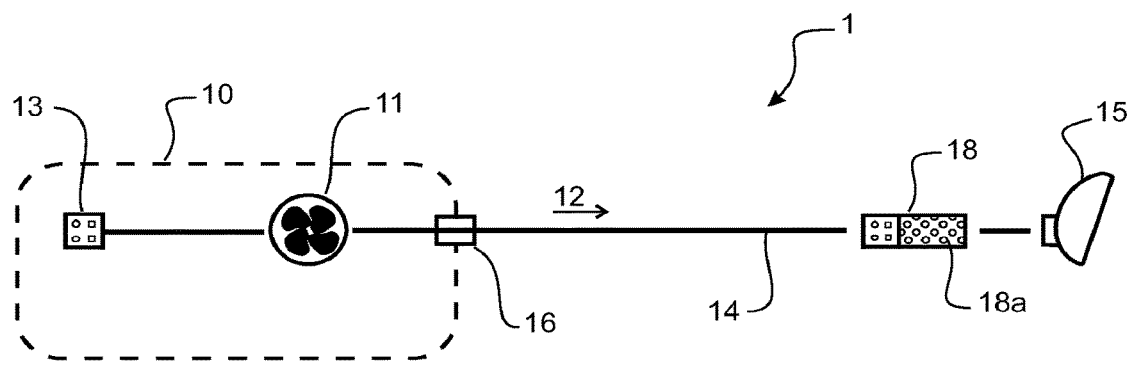
FIG. 1 is a schematic diagram of a breathing system with an adjustable HME.

FIG. 1 shows a schematic diagram of a breathing assistance system 1 for delivering pressurised humidified air and/or a flow of humidified air to a patient to assist with breathing. The system 1 comprises a breathing apparatus 10 with a blower 11 that generates a flow of air 12 using a fan or similar that draws on ambient (inlet) air. The breathing apparatus could, for example (and without limitation) be a CPAP, bi-level, autotitration or NIV apparatus. Details of these apparatus are known to those skilled in the art and need not be described further here. The system 1 (or breathing apparatus 10 itself as shown in FIG. 1) can comprise an inlet filter for filtering inlet air. The system also comprises a breathing conduit and patient interface 15 (such as a mask or cannula) for delivering the air 12 to the patient. The conduit 14 connects to an outlet 16 of the blower 11/breathing apparatus 10. The system also comprises an adjustable heat and moisture exchanger (HME) 18 with bias flow holes coupled between the conduit 14 and patient interface 15 for humidifying the air 13 being delivered to the patient. In alternative embodiments, the HME could be integrated into or attached in or to the patient interface 15. The HME comprises HME material 18a. While the assembly in FIG. 1 is termed a "breathing assistance system" it will be appreciated that the term "breathing apparatus" can also be used generally to refer to the breathing apparatus itself in combination with the peripheral components (such as conduit, HME and patient interface). As such, the terms "breathing assistance system" and "breathing apparatus" can be used interchangeably.

An HME comprises an HME material that works generally as follows. Inlet airflow passes through the HME material such as a porous material such as foam, paper, or a substance that acts as a condensation and absorption surface often impregnated with hygroscopic salts such as calcium chloride, to enhance the water-retaining capacity. As the patient inspires (inlet airflow), the heat and water from the patients' previously expired breath (patient airflow) are released from the HME material into the inlet airflow and so condition the inspired air by humidifying and heating it. Embodiments described herein could use new HME materials described herein, or HME materials known to those skilled in the art.

Adjustable HMEs

Various embodiments of adjustable HMEs are described, including embodiments that involve adjusting the airflow through the HME and/or HME material to adjust or control humidity.

A preferred humidity of air provided to a patient, from a therapy or health perspective, is around 25 mg/L to 32 mg/L of water. However, a patient may prefer less humidity depending on their preference for how comfortable it feels to breathe highly humidified air. Additionally, 100% relative humidity can cause rainout in the patient interface or conduits, so it may be appropriate to deliver, for 85% relative humidity at 34° C., which is what a patient's breath is at.

Further, an HME's effectiveness at providing humidity may depend on the surrounding environment. For example, performance may be negatively affected by cold ambient temperatures, say a cold bedroom. In such a situation, an HME may deliver a sub-optimal humidity. As the room temperature rises, an HME may become more effective, possibly too effective, causing rainout in the patient interface. Therefore, the difficulty with prior art (non-adjustable) HMEs is that often they work too well (or not well enough) and provide a humidity above (or below) that which is required.

HME with Reconfigurable HME Material

An adjustable HME 18 according to the presently disclosed subject matter used in a breathing system such as that of FIG. 1 enables the humidity of the delivered air to be adjusted to a suitable or preferred (comfortable) level. To be able to adjust the humidity provided by the HME 18 depending on the external temperature conditions or preference is advantageous. The preferred humidity of air provided to a patient with breathing disorders, from a therapy perspective, is 25-32 mg/L of absolute humidity. However, patients may wish to adjust the amount of humidity provided due to environmental conditions or personal preference, and may wish to do this on a daily basis. The difficulty with prior art HMEs is that often they provide a humidity above that which is required and cannot be adjusted.

Figure 2:
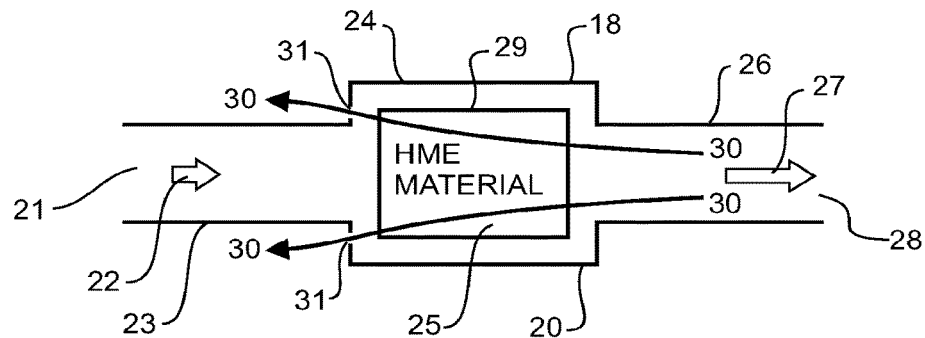
FIG. 2 is a schematic diagram of an adjustable HME.

Referring to the non-limiting exemplary embodiment in FIG. 2, in general terms, the adjustable HME 18 comprises a housing 20 with an inlet 21 for receiving inlet air flow 13 from the breathing apparatus 10 (usually indirectly via the breathing conduit 14 although it could be directly coupled to the outlet 16 of the breathing apparatus). The inlet 21 can also be termed "breathing apparatus inlet". Inlet air 21 passes through an inlet duct 23 creating an inlet air flow path 22. The inlet air flow path leads to an HME chamber 24 comprising a suitable HME material 25 (such as any described in this specification, or any known to those skilled in the art) and air flowing through picks up heat, humidity, and/or moisture from the HME, after which the air flow flows through to an outlet duct 26 creating an outlet air flow path 27, for air that flows to an outlet 28 for coupling to the patient interface 15 for delivering humidified air 27 to the patient. The patient exhales air 30. This travels through the outlet duct 26 and outlet flow path 27 through the HME material 25 and out the bias flow holes 31 to ambient air (and/or back through the inlet duct 23 if the pressure is low). As exhaled air passes back through the HME, at least a portion of heat, humidity and/or moisture of the exhaled air is retained by the HME. The bias flow holes 31 are placed distal to the patient after the HME material 25 with respect to patient airflow. This is so that the patient airflow passes over the HME material before passing to ambient though the bias flow holes. As such, the outlet air flow path 27 and outlet duct 26 can also be termed the "patient air flow path" and "patient duct" respectively when transferring patient air as air can travel in both directions. The inlet air flow (path), outlet air flow (path), and patient air flow (path) together form the air flow (path) for the HME. The terms "inlet" and "outlet" can also be used more generally refer to the inlet/outlet air flow (paths) and/or ducts where context allows.

As the inlet 22 and patient 30 air flows travel past the HME material 25, they contact opposite surfaces of the HME material 25 and humidity from the patient air flow 30 is disposed in the inlet air flow 22 to humidify the air 27 delivered to the patient. An adjuster 29 allows adjustment of configuration of the HME material 25 and/or inlet/patient air flow paths 22, 30 to adjust the amount of humidity exchanged. The HME material 25 can take many configurations. The HME material configuration, and in particular the surface area contacting the inlet 22 and patient 30 air flows can be adjusted to increase/decrease the surface area to increase or decrease the humidity exchange, thus adjusting the humidity of the outlet air 28 delivered to the patient. Alternatively or additionally, the HME material configuration can be adjusted to control the volume/level of inlet 22 and patient 30 air flows presented to the surface of the HME material 25, thus adjusting the humidity of the outlet air 28 delivered to the patient. Altering the HME configuration in any manner to alter: a) the surface area of HME material presented to air flows, b) airflow rate, c) volume of air presented to the surface area, and/or d) residence time of the airflow on the surface area of the HME can alter the humidity provided. Generally, the HME configuration controls the amount of airflow that bypasses the HME or HME material to control the level of humidification.

Possible Arrangements of HME with Adjustable HME Materials

Figure 3A:
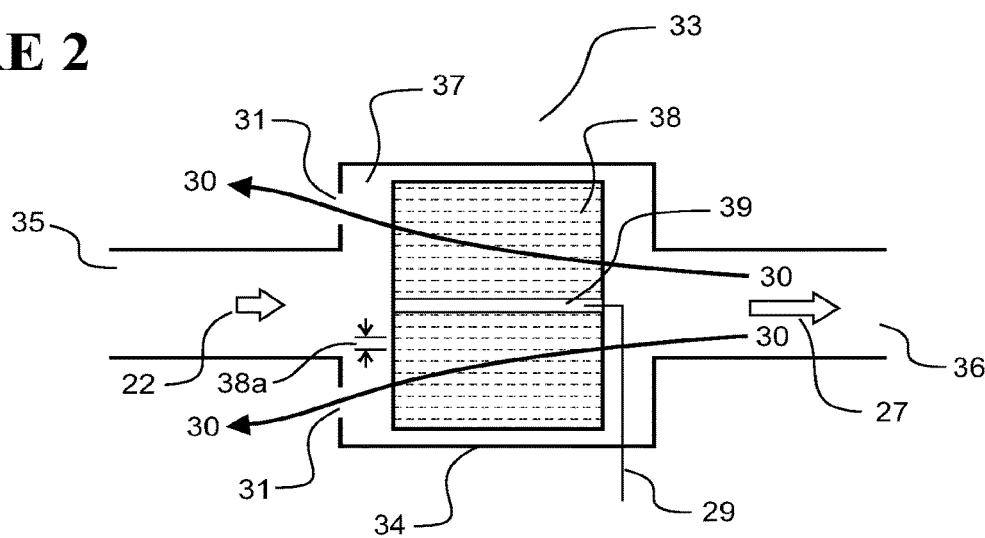
FIGS. 3a to 3e show a one embodiment of an adjustable HME.

FIGS. 3a, 3b, 3c, 3d, 3e show an adjustable HME according to one non-limiting exemplary embodiment that can be used in the system of FIG. 1 and follows the general model shown in FIG. 2. FIG. 3a is a schematic indicative of the embodiment for explanatory purposes, while the remaining FIGS. 3b-3e are possible physical embodiments. The adjustable HME 33 comprises a housing 34 (see FIGS. 3a, 3c) with an inlet 35 for connection to the breathing conduit 14 (see e.g., FIG. 1), a patient outlet 36 for connection to the patient interface 15, and bias flow holes 31. The bias flow holes 31 are at the distal end of the HME with respect to the patient, after the HME material. In this configuration, exhaled patient airflow laden with humidity passes over or through the HME material prior to passing through the bias flow holes 31 to ambient. Adjustable HME 33 also comprises an HME chamber 37, or similar, comprising HME material 38, which is generally in a sheet-like form that is spiral wound on a spindle 39, or similar. Inlet air flow 21 passes through gaps 38a formed between successive layers (shown as dotted lines in FIG. 3a) of the spiral wound HME material 38 to contact the surface of that material, where it is humidified and/or heated, then passed as outlet air flow through patient outlet 36 to the patient. Likewise, patient air flow 30 can pass through the gaps 38a between successive layers of the spiral wound HME material 25 to contact the surface of that material.

Humidity in the patient air flow 30 contacts the surface(s) of the HME material 38, and is "deposited" on the surface. That is, the HME material acts as a condensation and absorption surface that absorbs the humidity. Heat and water from the patients' previously expired breath are released from the HME material into the inlet airflow 22 and so condition the inspired air 22 by humidifying and heating it. The inlet air flow 22 contacts the surface(s) of the HME material 38 and picks up the humidity deposited by the patient airflow 30 as the heat and water from the patients' previously expired breath (patient airflow) are released from the HME material into the inlet airflow.

To adjust the level of humidity or moisture exchanged, and thus the humidity delivered to the patient, the spindle 39 can be rotated (e.g., clockwise or counterclockwise) using the actuator 29 to tighten and loosen the spiral wound HME material 38. This increases and decreases the gap 38a size respectively, and/or the size (e.g. diameter) of the spiral overall, which in turn alters the volume of inlet, outlet and patient flows presented to the HME material, which in turn alters the humidity transferred.

Figure 3B:
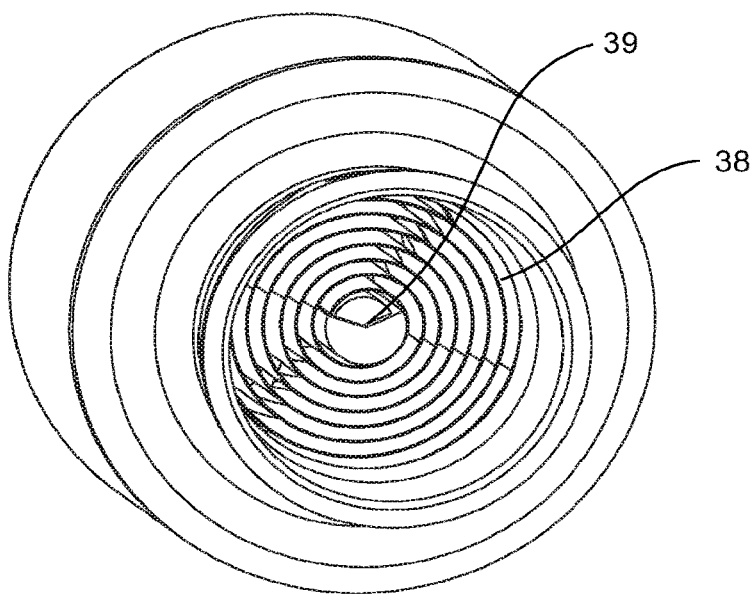
Figure 3C:
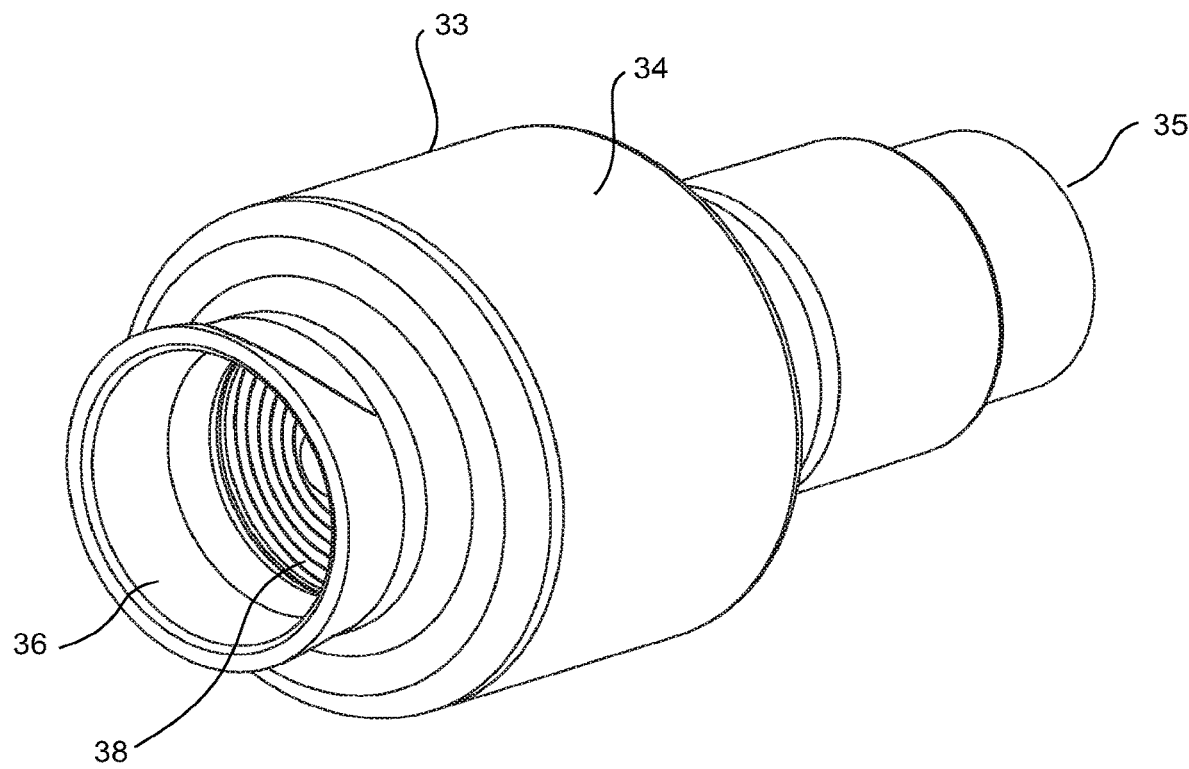
Figure 3D:
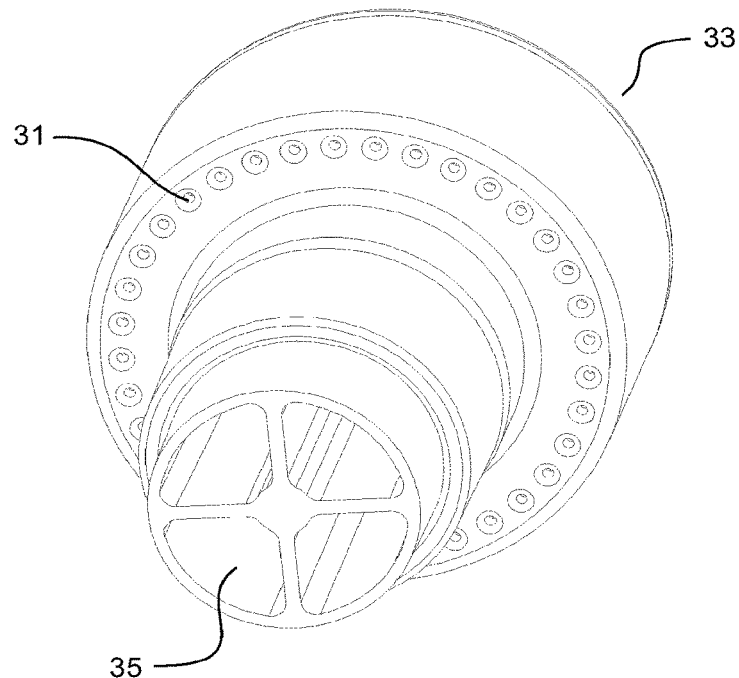
Figure 3E:
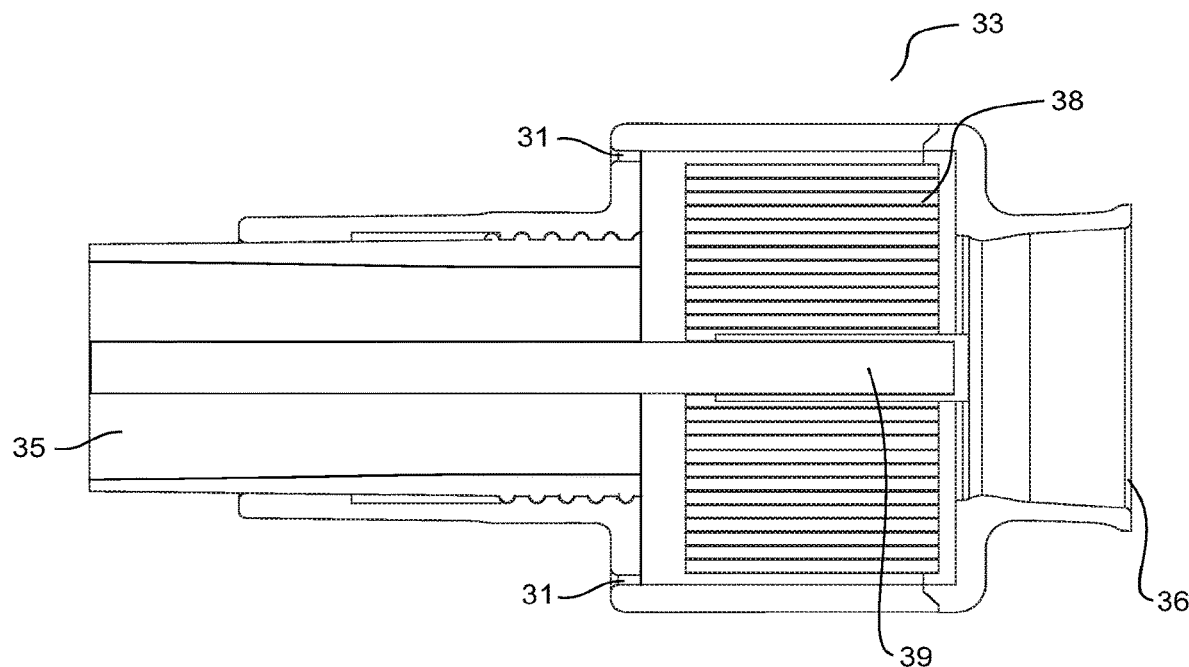
Figure 8A:
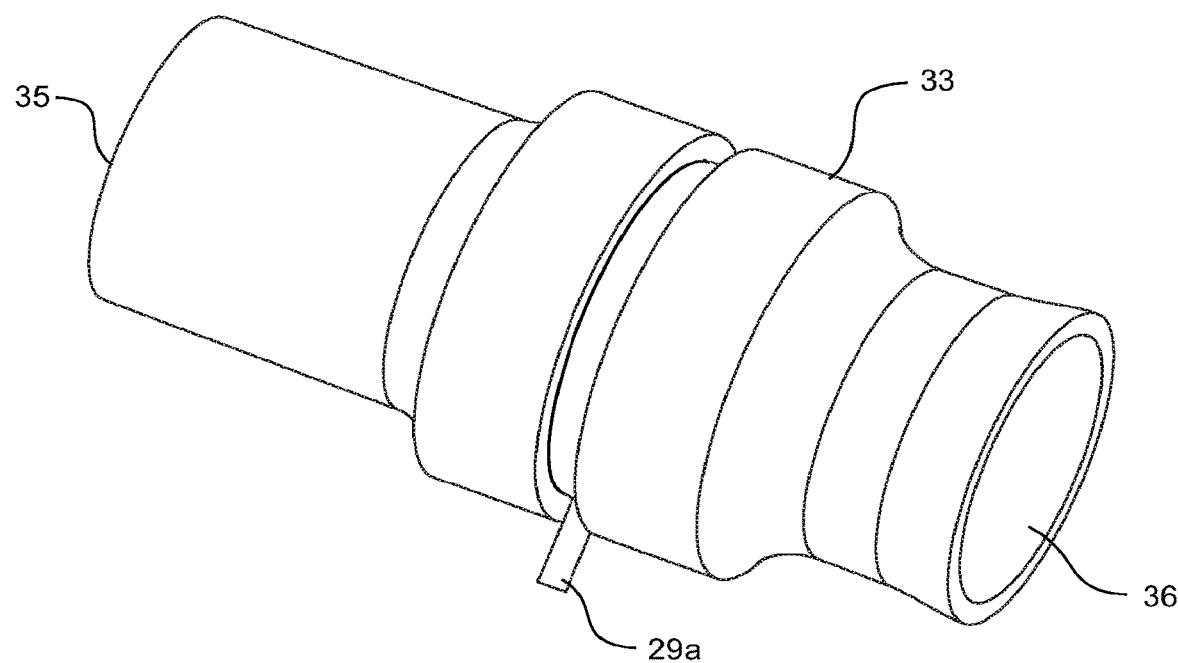
FIGS. 8a, 8b show a variation of the first embodiment shown in FIGS. 3a to 3c.
Figure 8B:
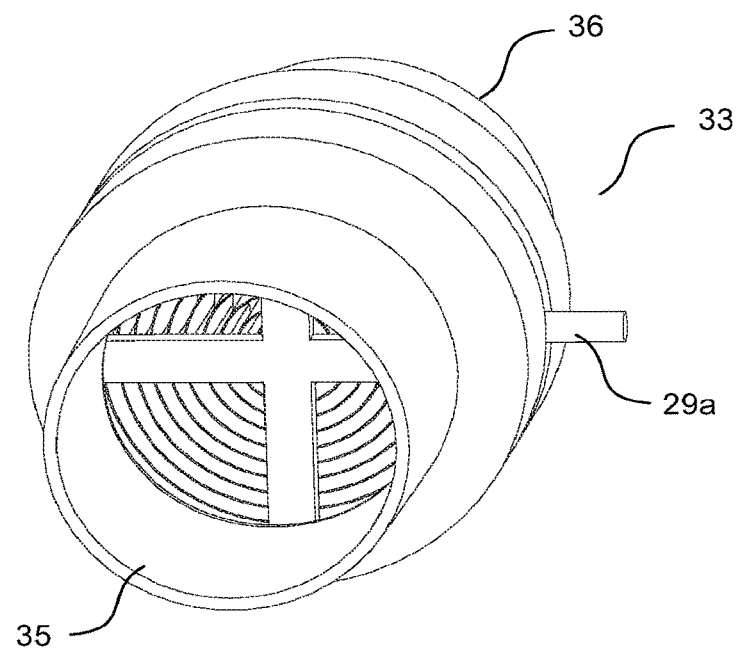

FIGS. 8a, 8b show additional non-limiting embodiments or variations of the embodiment shown in FIGS. 3a to 3c. As shown, a lever 29a is provided to adjust the configuration of the HME material. Lever 29a is connected to spindle 29 (not shown), and when the lever is moved, spindle 29 is rotated, and the HME material is reconfigured in a manner similar to that described with respect to FIGS. 3a to 3c.

Depending on the configuration of the spiral and/or the spindle, different humidity control effects can be achieved. By way of non-limiting example, referring to FIG. 5a, tightening the spiral 38 completely (or almost completely) narrows the gaps 38a between HME material 38 winding layers until little or no air can pass through. The inlet 22 and patient airflow 30 go around the HME material 38 as shown. This eliminates or at least substantially reduces the inlet 22 and patient 30 airflows that contact the surface area of the HME material 38, thus eliminating or substantially reducing hear and/or humidity that is transferred to the inlet flow 22, which in turn reduces the humidity of the inlet flow 22.

Figure 5A:
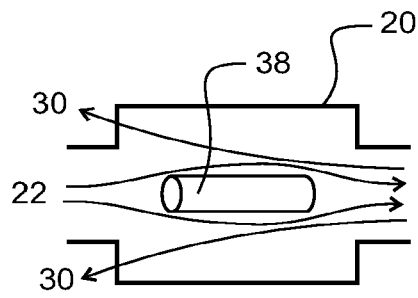
FIGS. 5a to 7b show variations of the configuration and control of the HME of FIGS. 3a to 3c.
Figure 5B:
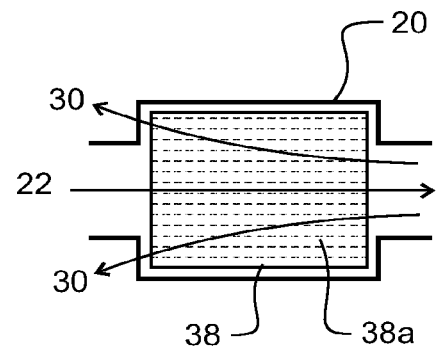

In contrast, as shown in FIG. 5b, loosening the spiral (by rotation) increases the gaps 38a between the spiral windings and allows inlet 22 and patient airflow 30 to pass through the gaps. This allows for the transfer of heat and/or humidity from the patient airflow 32 the inlet airflow 22, thus increasing the humidity of the inlet airflow 22. The more that the spiral is loosened, the bigger the gaps 38a, bigger gaps increase airflow through the gaps and/or increase the surface area of the HME material 38 that is exposed to the airflows 22, 30. This in turn, increases the transfer of heat and/or humidity from the patient airflow 30 to the inlet air flow 22, which increases the overall humidity of the inlet air flow 22.

Depending on the configuration of the spiral 38 and the operation of the spindle 29, loosening and tightening the spiral may have a different effect to that described with reference to FIGS. 5a, 5b.

Figure 6A:
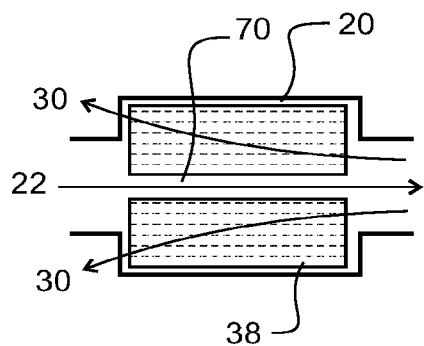

Referring to the non-limiting exemplary embodiment shown in FIG. 6a, if the spindle is loosened (e.g., by rotation) in a manner to open a central hole 70 (gap/aperture) but not increase the gap size between spiral layers e.g. 38a, then the airflow (inlet 22 and patient 30) may stay the same (or decrease slightly) but there will be little or no surface contact with the HME material. This will eliminate or at least substantially reduce the transfer of humidity from the patient airflow 32 the inlet airflow 22, thus reducing the humidity of the inlet airflow 22.

Figure 6B:
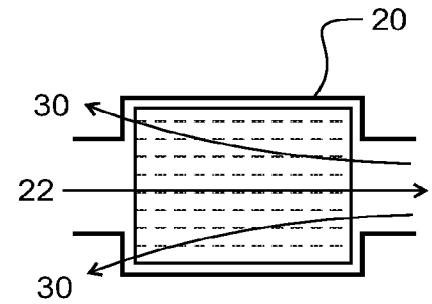

In contrast, referring to an adjusted configuration shown in FIG. 6b, tightening the spindle closes the central hole 70, which actually increases the gap e.g. 38a between spiral layers as the gap spacing expands to fill in the central hole 70. The actual airflow (inlet 22 and patient 30) may stay the same (or increase slightly), however, due to an increase in the gap between spiral layers 38a, the airflows are in contact with more surface area of the HME material. This increases transfer of humidity from the patient airflow 32 to the inlet airflow 22, thus increasing the heat and/or humidity of the inlet airflow 22.

Figure 7A:
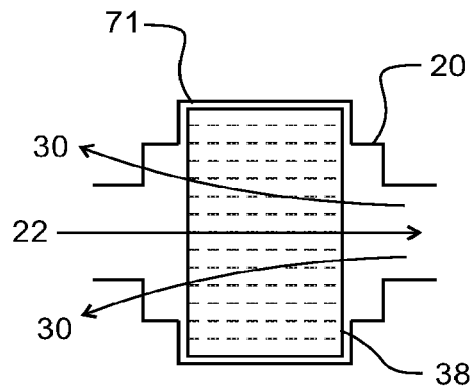
Figure 7B:
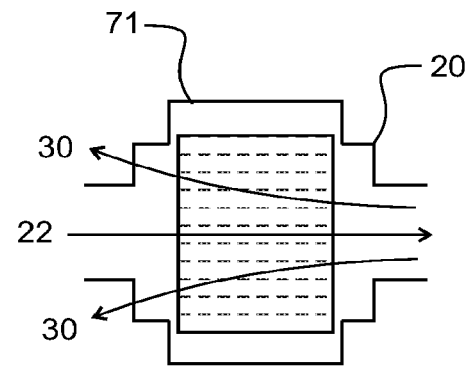

Yet another non-limiting exemplary embodiment is shown in FIGS. 7a, 7b. In this embodiment there is an annular recess 71 in the chamber that is removed from the airflow path 22, 30. Referring to FIG. 7a, if the HME spiral 38 is loosened, some of the spiral layers will expand into the annular recess 71. This will reduce the number of layers (and therefore surface area) of the HME material 38 that is in the airflow 22, 30. This will reduce the amount of heat and/or humidity transferred from the patient airflow 30 to the inlet airflow 22, thus reducing the humidity of the inlet airflow 22. In contrast, referring to FIG. 7b, if the HME material spiral 38 is tightened, the layers of HME material will be retracted from the recess 71 back into the airflow 22, 30. This will increase the number of layers (and therefore surface area) of the HME material that is in the airflow 22, 30. This will increase the amount of heat and/or humidity transferred from the patient airflow 30 to the inlet airflow 22, thus increasing the heat and/or humidity of the inlet airflow 22.

In all the examples above, the tightening, loosening, rotating or retracting of the HME material can be controlled to differing degrees, which correspondingly affects the amount of humidity transferred to the inlet air flow. Other configurations might have other humidity control effects, and the examples above are exemplary only.

FIGS. 4a, 4b, 4c, 4d show an adjustable HME 41 according to another non-limiting exemplary embodiment that can be used in the system of FIG. 1. The adjustable HME 41 comprises an inlet 43 for connection to the breathing conduit 14 and an outlet 42 for connection to the patient interface 15. The inlet and outlet are joined by a central passage 44 comprising an outlet (patient) duct 44b and inlet duct 44a that are coupled to each end of an HME material chamber 44c to create an air flow passage. The HME material chamber 44c comprises bias flow holes 45 located between material chamber 44c and inlet 43. As shown, adjustable HME 41 also comprises layered HME material 46, such as a spiral, or an HME material in sponge form. Under fully open conditions, inlet airflow passes through the inlet 43 through the HME material and to the outlet 42 to the patient.

Figure 4A:
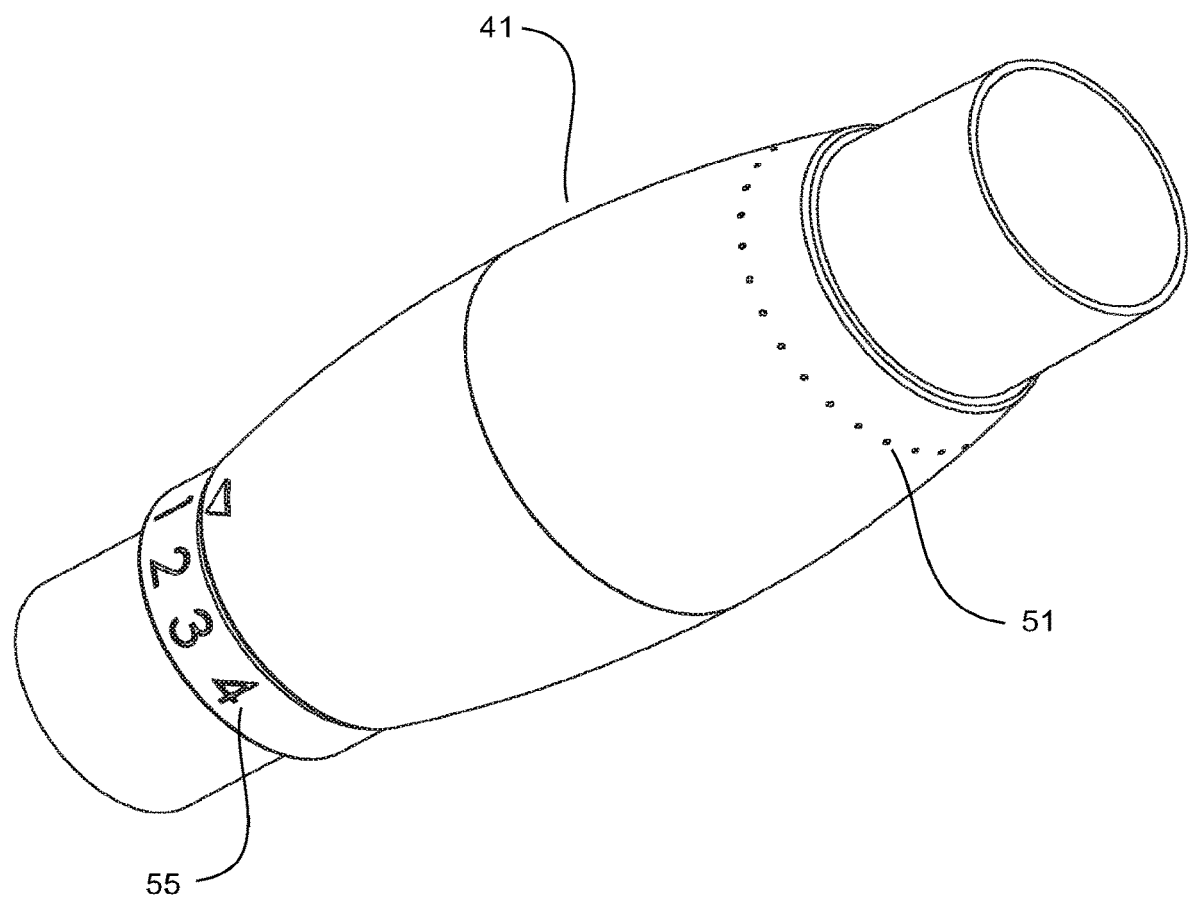
FIGS. 4a to 4d show another embodiment of an adjustable HME.
Figure 4B:
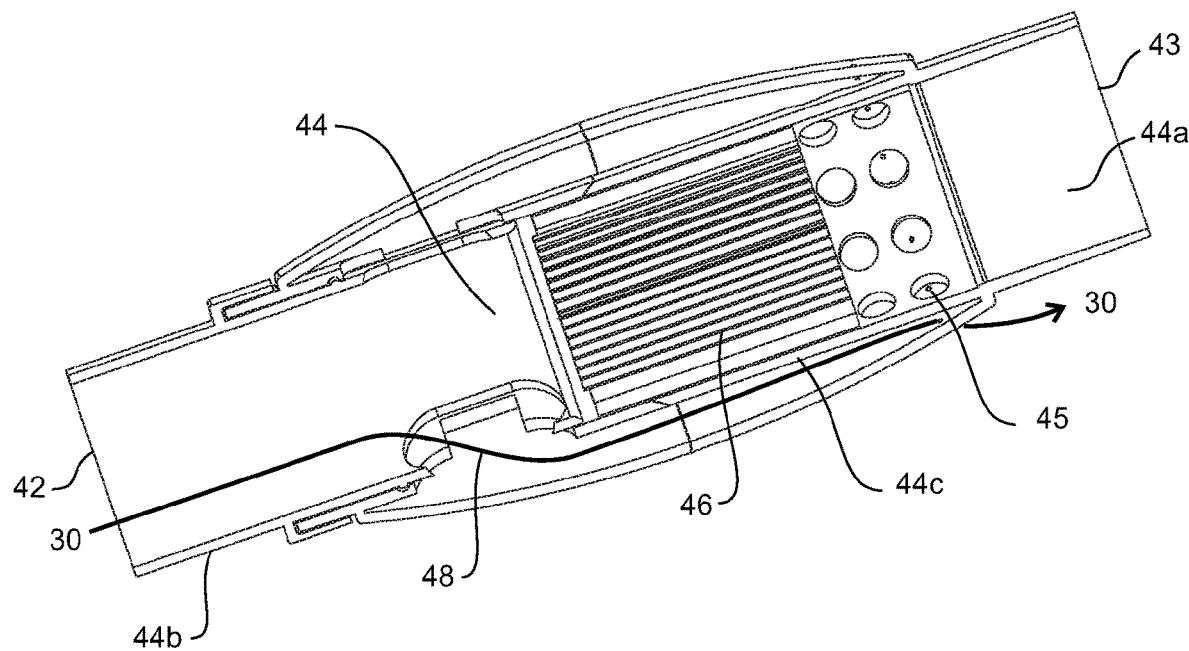

The chamber comprises a tubular extension 47 (see FIG. 4c) with an aperture 48 (see FIG. 4b). The outlet/patient duct 44b or at least part of it sits within the tube extension 47 so that the tubular extension can rotate coaxially within it. The outlet duct 44b has an aperture 49 that fully or partially aligns, or does not align at all with the tubular extension aperture 48 depending on the relative rotational positions of the outlet duct 44b and tubular extension 47. The outlet duct aperture 49 and tube extension aperture 48 form an air flow valve.

As shown in the non-limiting exemplary embodiment, the HME 41 comprises a curved outer housing in two parts. The first part 50a is fixed to/integrated with the inlet duct 44a and has (housing) bias flow holes 51. The orientation shown in FIG. 4b allows for passage of patient air 30 that passes from the interior of the inlet 44a, through the HME chamber 44c through the HME chamber bias flow holes 45 and out to ambient. The second part 50b is rotatable relative to the first part 50a and is coupled to or is integrally formed with the tubular extension. As shown, in this embodiment, the second part 50b is integrally formed with the tubular extension. One end 47a of the tubular extension sits in and rotates within a skirt/annular collar 53 extending from and forming an annular channel/collar around the outlet duct 44b. Rotating the second part 50a rotates the tubular extension 47 relative to the outlet duct 44b, thus altering the relative aperture 48, 49 alignments. Altering the relative alignments alters the combined aperture size and the volume of air flow 30 from the outlet/patient 44b duct through the apertures 48, 49, through the HME chamber 44c and material 46 and through the bias flow holes 45, 51 and inlet duct 43, and vice versa.

Figure 4C:
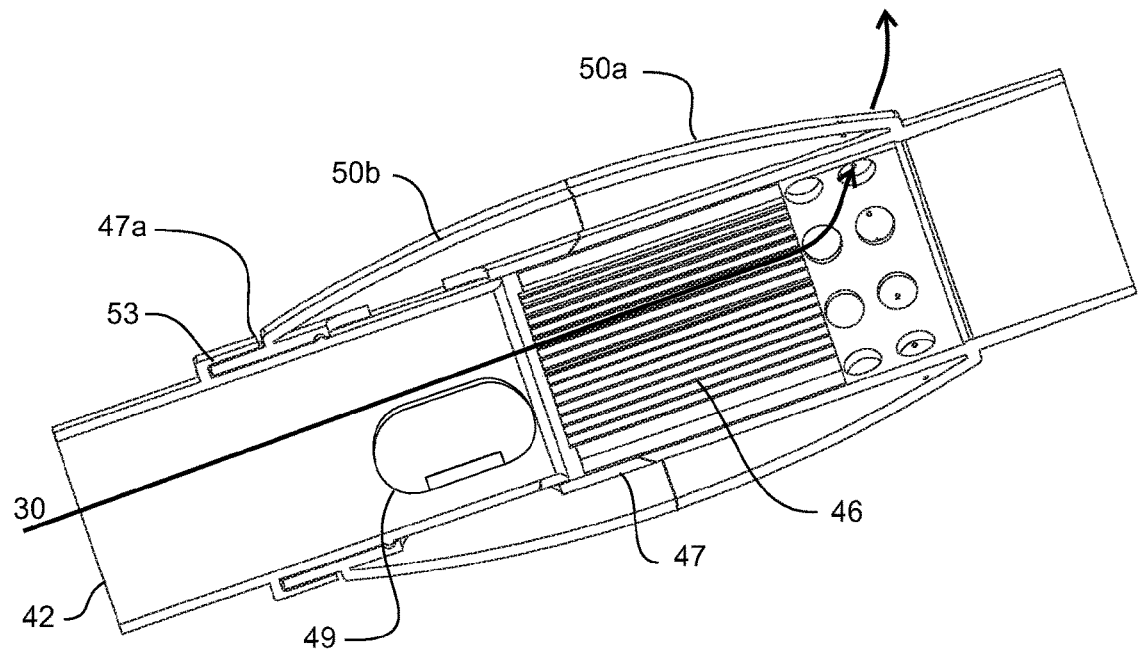
Figure 4D:
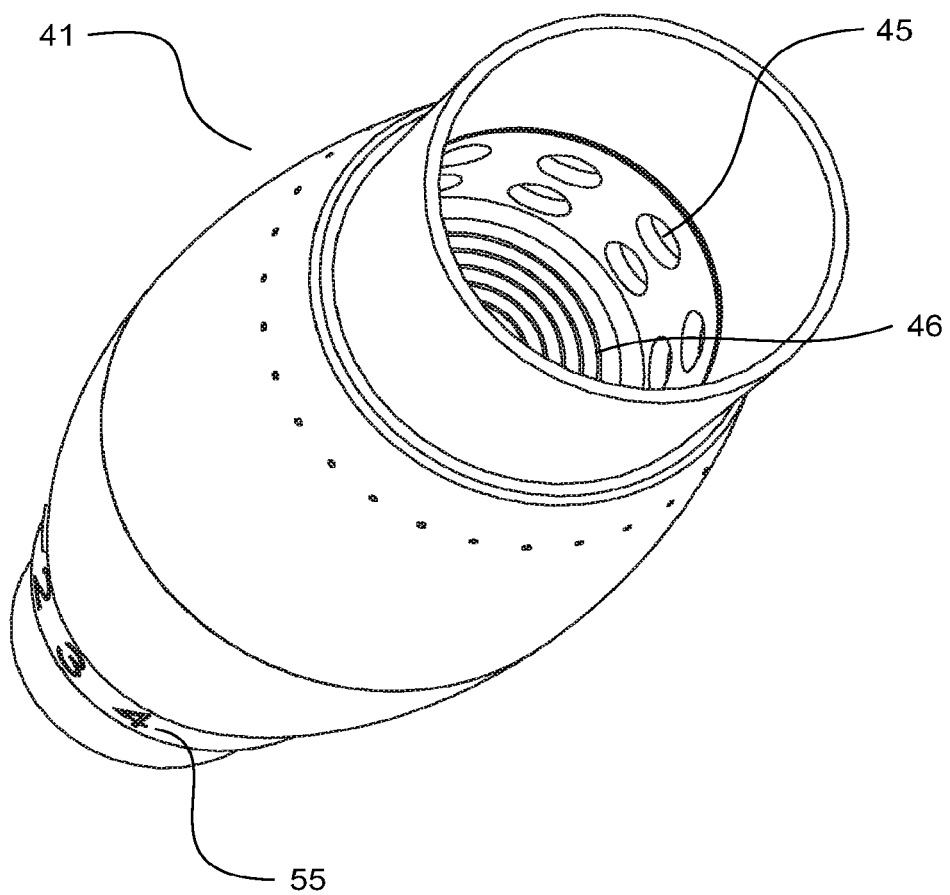

Altering the flow 30 alters the level of inlet 22, outlet 28 and patient 30 flows that contact the surface of the HME material 46, thus altering humidity exchange. For example, as shown in FIG. 4c when the apertures 47/48 are completely unaligned, all or substantially all air from the patient flows through the outlet 42 through the HME material where it deposits humidity to be collected by the inlet flow and passes out the bias flow holes 45, 51. This provides maximum humidity to the inlet airflow. When the apertures 49/48 are complete aligned, as shown in FIG. 4b, at least a portion of exhaled patient air 30 is directed around to bypass the HME chamber 44c and bypass the HME material 46 and instead flow around within the outer curved housing 50a, 50b and out the bias flow holes 45, 51. This reduces or eliminates heat and/or humidity available to the inlet flow.

Additionally, it is possible to partially align the apertures 49, 48 whereby some of the patient airflow passes through the HME material and some bypasses it—thus provide humidity between the maximum and minimum. Humidity level is controlled by controlling the degree to which the apertures 49, 48 are aligned (thus increasing or decreasing the combined aperture size and controlling how much patient flow goes through the HME material versus bypassing it). Indicia 55 (see e.g., FIGS. 4a and 4d) could be placed on the first 50a and/or second 50b part of the housing to guide a user on how much to rotate the second part to adjust humidity to the desired level. The inner duct can optionally be rotated to align the apertures instead of rotating the outer duct.

Other variations and embodiments are possible also. For example, a water filled/impregnated sponge can be added to the HME for extra humidity in high mask or mouth leak situations. A heated or insulated HME and mask connection tube variant would work better at lower temperatures.

In another variation to FIGS. 4a-4d, the HME material could be on the periphery of a central duct in an annular arrangement and the air flow directed through the annular periphery for full humidification, through the open central duct for no humidification, or directed through both for a lower level of humidification.

HME with Reconfigurable Bypass Airflow Holes

By way of non-limiting example, generally the volume/level of inlet air 22 and patient air 30 flows, and hence the effectiveness of the HME material 25, is adjusted by controlling the volume of inlet air 22 and patient air 30 that bypasses the HME material 25. It is to be understood that higher volume flow of inlet air 22 and/or patient air 30 leads to increased uptake of humidity inside the HME material 25 and higher HME effectiveness. While, reduced volume flow of inlet air 22 and/or patient air 30 subsequently decreases uptake of humidity inside the HME material 25 and lower HME effectiveness.

Adjustment of inlet air 22 and/or patient air 30 flow can be achieved by altering the volume, surface area and/or position of the opened bias flow holes 31. For example, in a first configuration, bias flow holes 31 are open proximate the inlet duct 23 end, while closed at the outlet duct end 26. This configuration forces the entirety of the patient air 30 flow through the HME material 25 before passing through the bias flow holes 31, and provides higher levels of heat, moisture and/or humidity to be retained by HME material 25, thus provides for higher levels of heat, moisture, and/or humidity to be added to inlet air flow 22.

In a second configuration, bias flow holes 31 are closed proximate the inlet duct 23 end, while open at the outlet duct end 26. This configuration allows volume of patient air 30 flow to exit to ambient through the open bias flow holes 31 before reaching the HME material 25, thereby bypassing the HME and reducing levels of heat, moisture and/or humidity to be retained by HME material 25, thus provides for reduced levels of heat, moisture, and/or humidity to be added to inlet air flow 22.

In a third configuration, bias flow holes may be open on both the inlet duct 23 end and the outlet duct 26 end, thereby providing for a variable or medium level of heat, moisture and/or humidity to be retained by HME material 25, thus provides for variable or medium levels of heat, moisture, and/or humidity to be added to inlet air flow 22.

The volume or effective surface area of bias flow holes 31 may be equal on both ends. Alternatively one end may have a higher net volume of bias flow holes 31, for example the inlet duct 23 end may have a higher effective surface area of bias flow holes 31, or the outlet duct 26 end may have a higher effective surface area of bias flow holes 31. The effect of having bias flow holes on both sides reduces the overall volume of inlet air 22 and/or patient air 30 flow through the HME material 25, as the flows may pass through the respective bias flow holes and exit to ambient prior to reaching the HME material 25. The adjustment of the bias flow holes may be achieved through a number of configurations, such as through a slider or twister mechanisms, which will be further described in detail below.

Possible Arrangements of Reconfigurable Bypass Airflow Holes

Figure 13A:
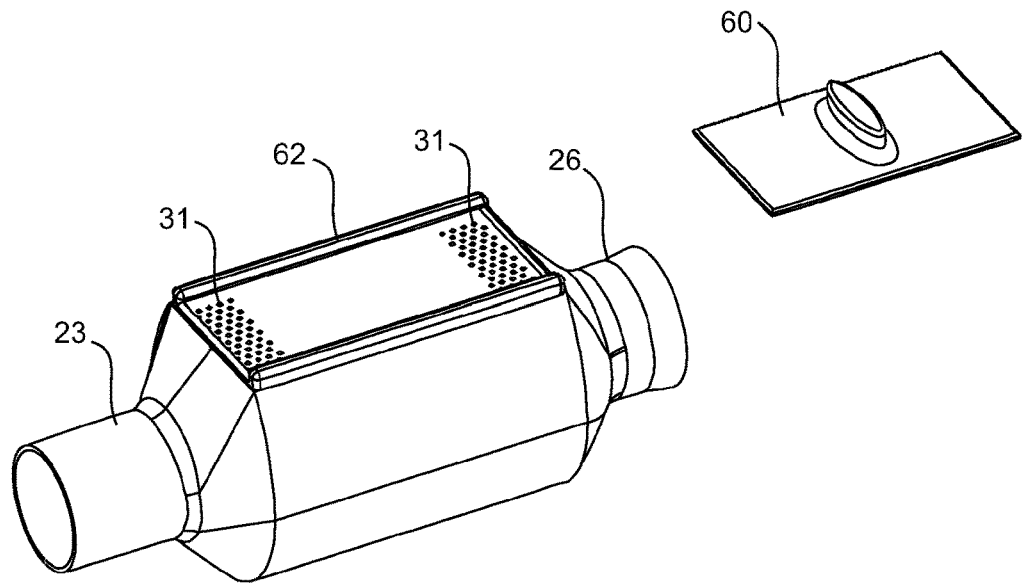
FIGS. 13a to 13d shows another embodiment of an adjustable HME.

FIGS. 13a to 13d show a non-limiting exemplary embodiment of an adjustable HME. FIG. 13a shows a HME having bias flow holes 31 on both ends of the HME material 25 and a track 62 for receiving a slider/cover 60. The slider 60 may be adjusted across a number of configurations to cover the bias flow holes to varying degrees to alter the effective open surface area of the bias flow holes to adjust the effectiveness of the HME.

Figure 13B:
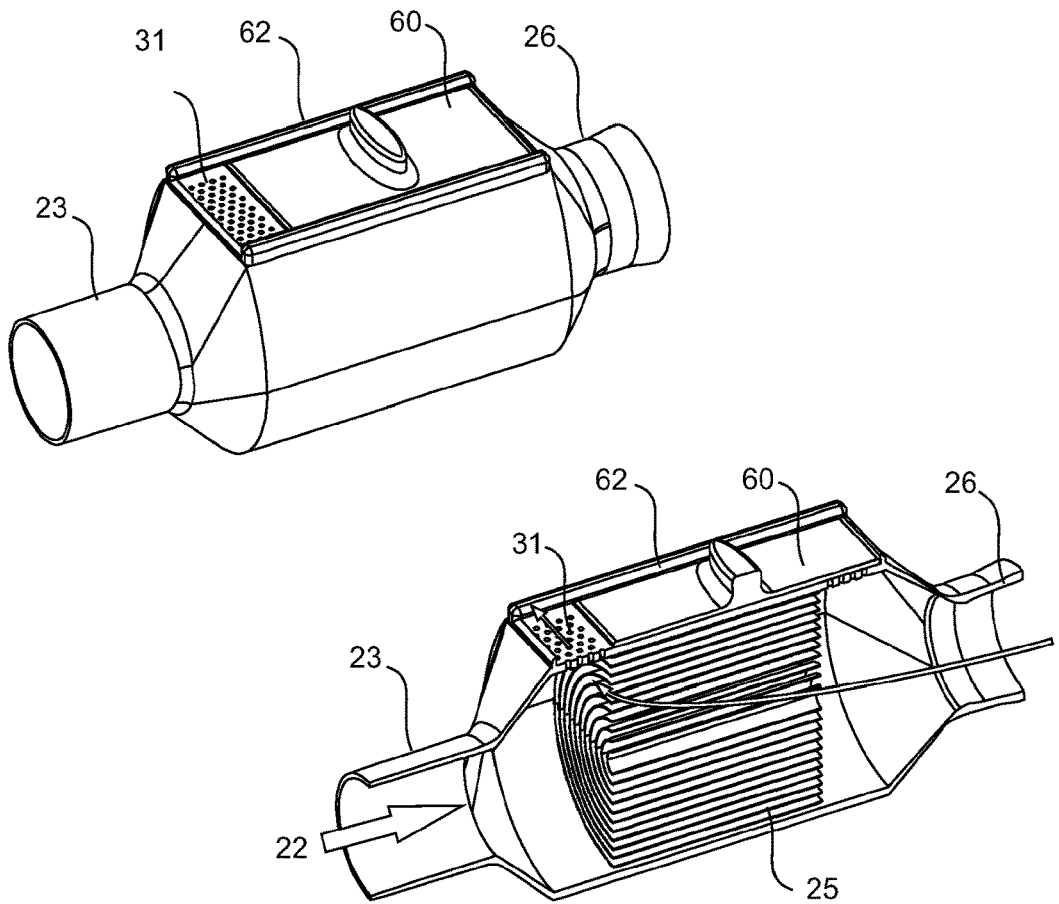
Figure 13C:
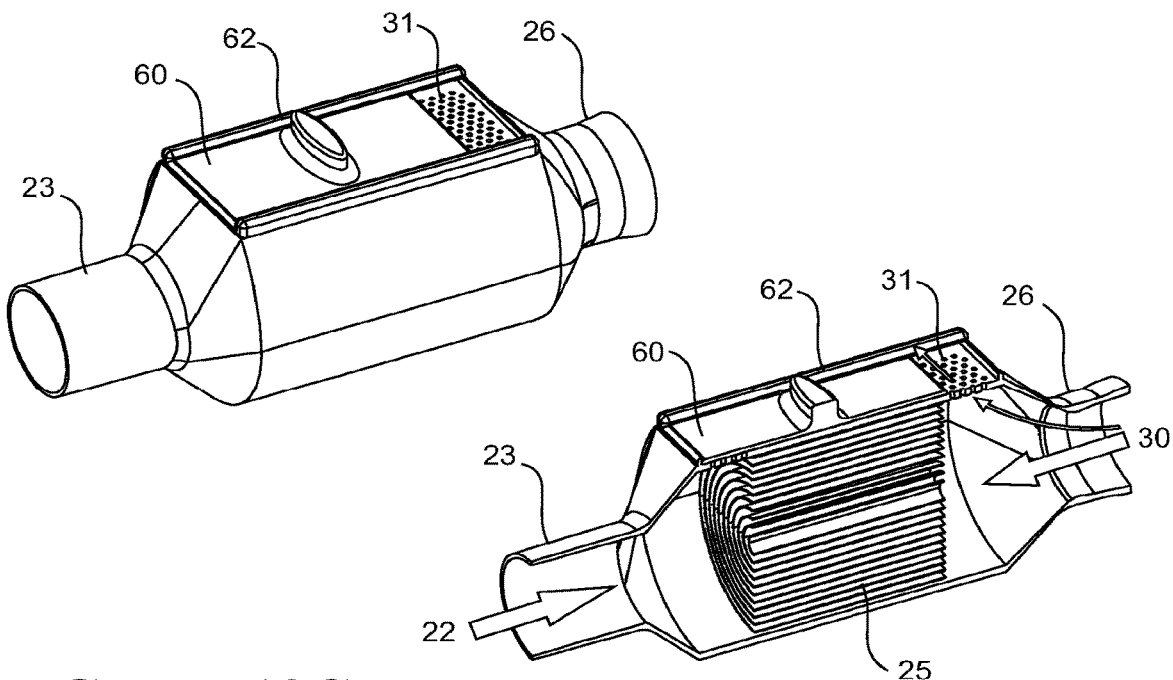
Figure 13D:
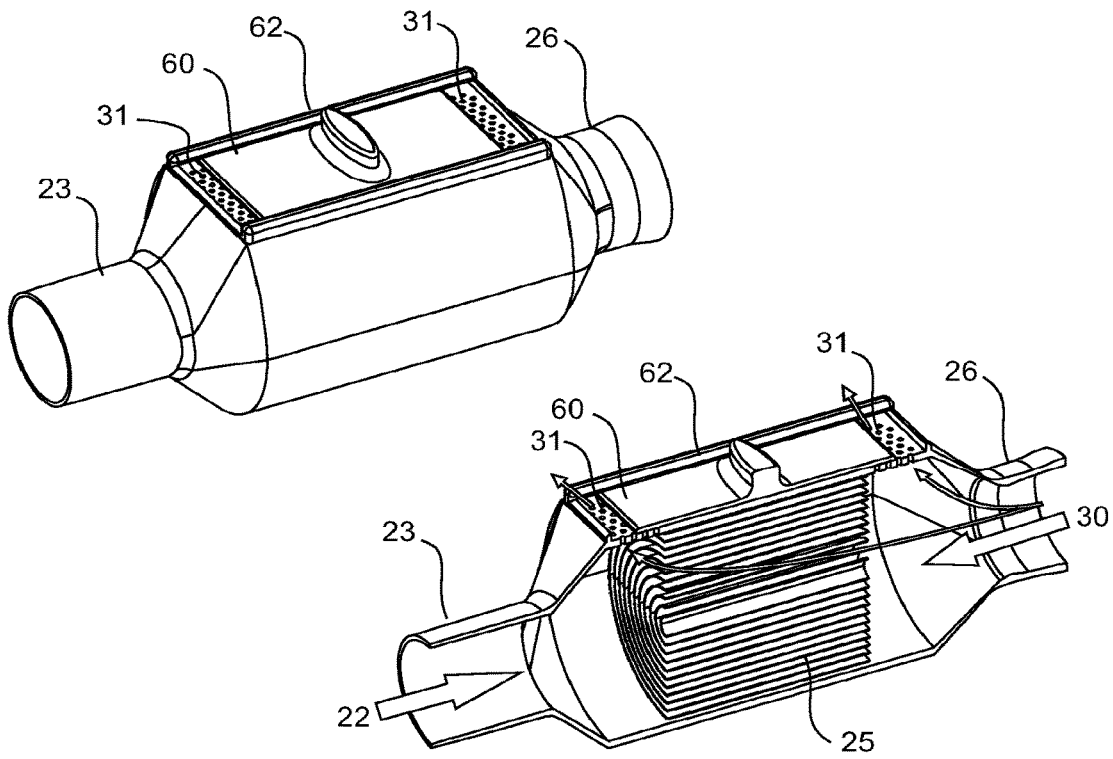

FIGS. 13b to 13d shows the HME in three configurations: 1) where the slider is adjusted to fully open bias flow holes proximal the inlet air duct 23 while fully close bias flow holes proximal the outlet air duct 26; 2) where the slider is adjusted to fully close the bias flow holes proximal the inlet air duct 23 while fully open bias flow holes proximal the outlet air duct 26; and 3) where the slider is adjusted to allow bias flow holes 31 on both sides of the HME material 25 to be open. FIG. 13d shows the surface area of bias flow holes 31 to be even across both sides of the HME material 25. It is to be understood that it is possible to adjust the slider such that bias flow holes 31 are open on both sides of the HME material 25 but with a net flow higher on one end. It is noted that the bias flow holes 31 and slider 60 may be dimensioned such that regardless of its configuration, a fixed surface area of bias flow holes 31 are always open to ambient. Advantageously, the effectiveness of the HME material may be adjusted without altering the volume of overall air flow to ambient, and without contributing to carbon dioxide build up inside the patient circuit.

In use, to adjust the level of humidity exchanged, and thus the humidity delivered to the patient, the slider 60 is adjustably moved along the slider track 62. The slider 60 functions by altering the effective surface area of the open bias flow holes 31 by closing (in the form of covering up) whole or portions of bias flow holes 31 on one side, while opening (in the form of uncovering) whole or portions of bias flow holes 31 on another side.

For example, in a first configuration, bias flow holes 31 are open proximate the inlet duct 23 end, while closed at the outlet duct end 26. This configuration forces the entirety of the patient air 30 flow through the HME material 25 before passing through the bias flow holes 31. As more exhaled patient air 30 flow passes through and deposits humidity on the HME material 25, this configuration provides higher amounts of heat, moisture and/or humidity to the inlet flow 22.

In a second configuration, bias flow holes 31 are closed proximate the inlet duct 23 end, while open at the outlet duct end 26. This configuration allows a portion of patient air 30 flow to exit to ambient through the open bias flow holes 31 before reaching the HME material 25, effectively bypassing the HME, reducing amount of humidity deposited on the HME material and therefore reducing the amount of heat, moisture and/or humidity available to the inlet flow 22.

In a third configuration, slider 60 is positioned such that bias flow holes are open on both the inlet duct 23 end and the outlet duct 26 end. This configuration provides a middle ground between either of the first two configurations, as patient air flow 30 is passed to both through ambient and the HME material 25. The slider 60 may also be adjusted such that there are even or uneven volume of open bias flow holes on either side of the HME material 25. The slider 60 may be adjusted according to any of the above configurations according to the desired humidity settings.

Figure 14A:
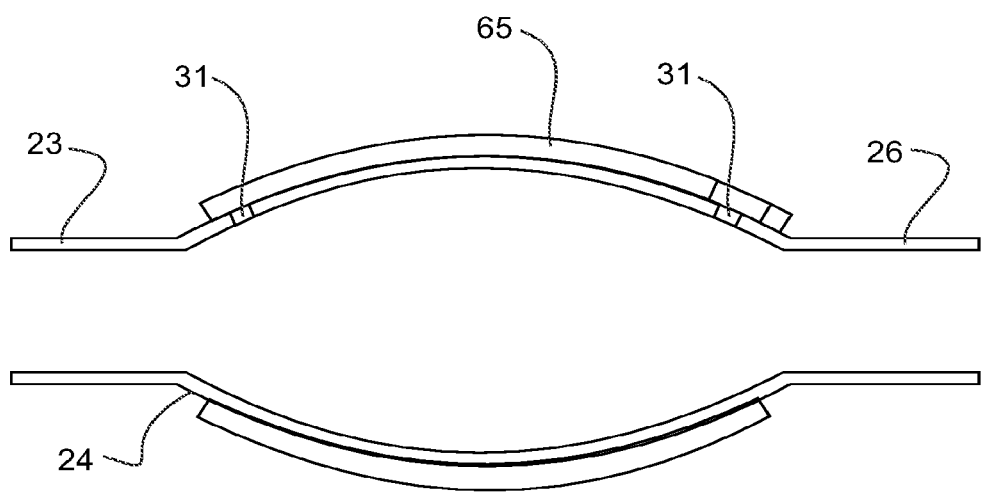
FIGS. 14a to 14c shows another embodiment of an adjustable HME.
Figure 14B:
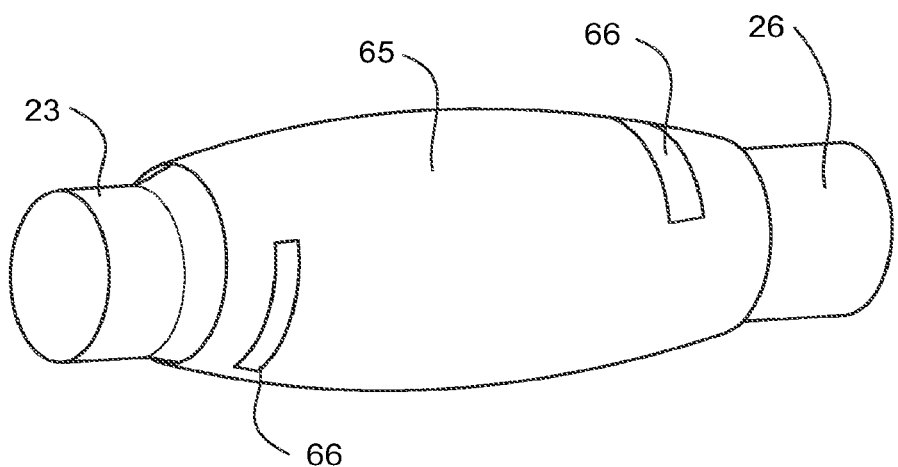
Figure 14C:
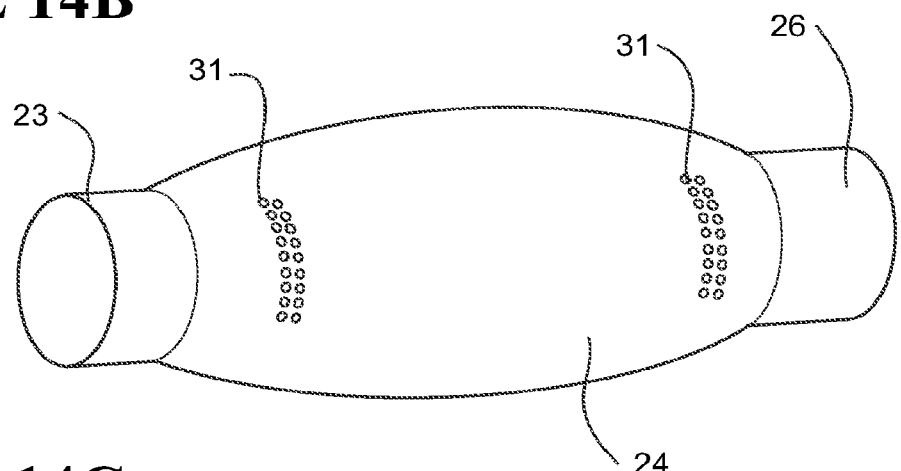

Other variations of the adjustable bias flow holes 31 are also possible. FIGS. 14a, 14b and 14c disclose another non-limiting exemplary embodiment of an adjustable HME. The HME comprises a tubular housing 24. The housing 24 includes a set of bias flow holes proximate the inlet duct 23 and a set of bias flow holes proximate the outlet duct 26, where the bias flow holes would be located on either side of a HME material 25. An outer shell 65 is coupled to the tubular housing 24 and rotatably movable in relation to the housing 24. The outer shell 65 is configured with apertures 66 to selectively cover or uncover the bias flow holes 31 as the shell 65 rotates relative to the housing 24.

In one configuration, the shell 65 is rotated to close the bias flow holes 31 proximate the inlet duct 22 and open the bias flow holes 31 proximate the outlet duct 26. In this configuration, more patient air 30 flow will exit to ambient and bypass the HME material 25, and thus reducing the amount of heat, moisture and/or humidity available to the inlet flow 22.

In another configuration, the shell 65 is rotated to open the bias flow holes 31 proximate the inlet duct 22 and close the bias flow holes 31 proximate the outlet duct 26. This configuration will have the effect of directing more patient air 30 flow through the HME material 25 before exiting the bias flow holes, thereby increasing the amount of heat, moisture and/or humidity available to the inlet flow 22

Various modifications of adjusting HME effectiveness through the adjustment of bias flow holes upstream and downstream of the HME material 25 will be apparent to those skilled in the art without departing from the nature of the invention.

Figure 15A:
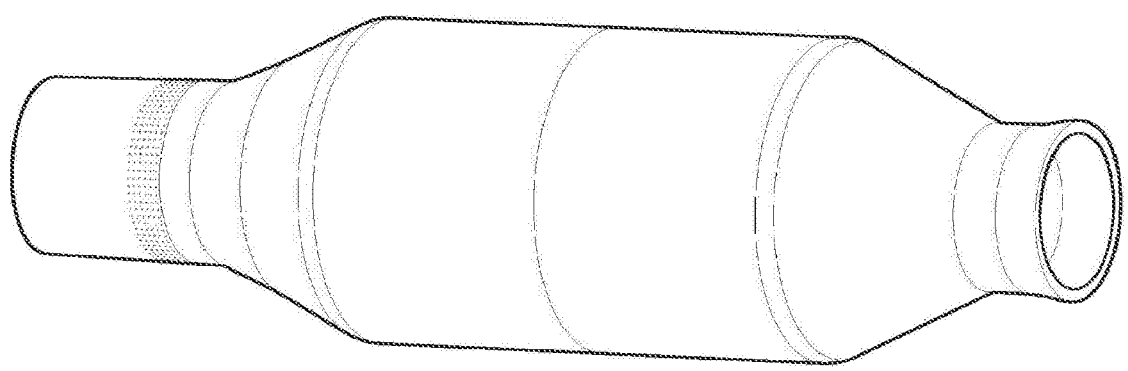
FIGS. 15a and 15b shows an adjustable HME with uniform bias flow holes.
Figure 15B:
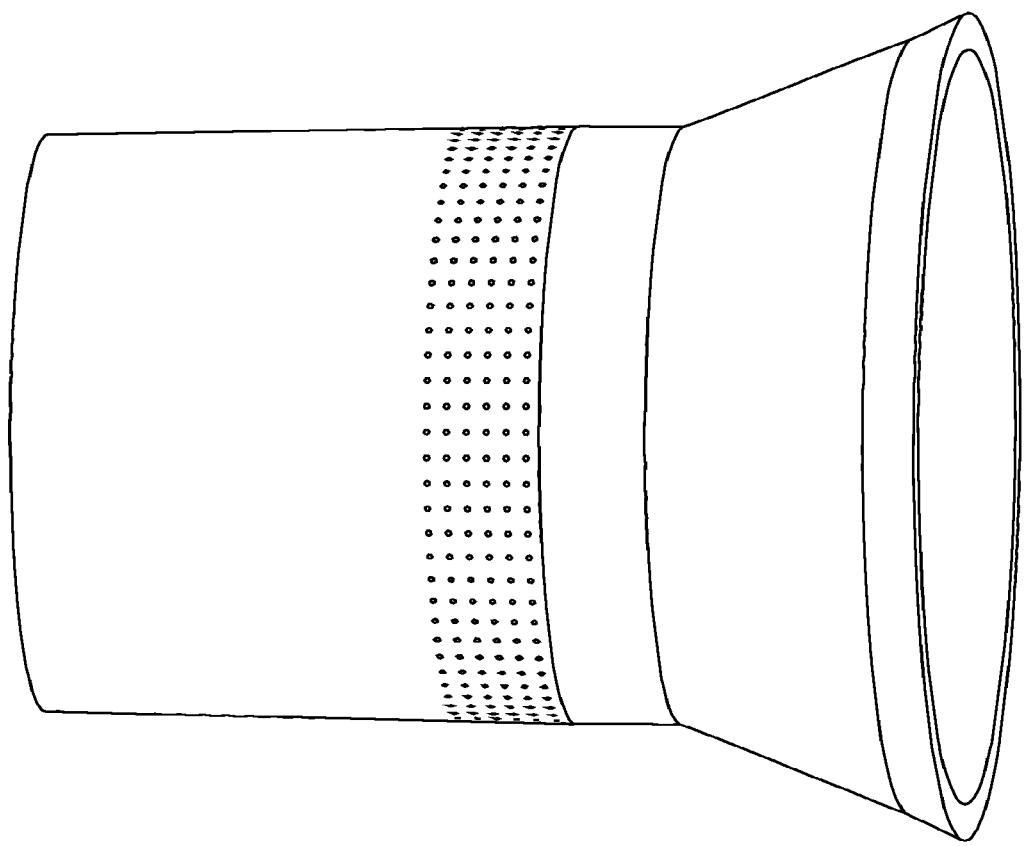

Referring to the non-limiting exemplary embodiment shown in FIGS. 15a and 15b, bias flow holes 31 for adjustable or non-adjustable HMEs as described above may be in the form of small and uniformly spaced configurations. For example, the bias flow holes 31 may be less than 1 mm in diameter and uniformly spaced partially or wholly across the perimeter of a HME housing. Preferably, the bias flow holes are less than 0.5 mm in diameter. More preferably, the bias flow holes are of 0.2 mm diameter.

Generally, such small bias flow holes provide for quieter bias flow with less entrained air or draft. However, such small bias flow holes are also more susceptible to being clogged by condensation, for example. Being located on the on the inlet side of the HME allows for smaller bias flow holes, because moisture that may clog such small bias flow holes is generally deposited or retained within the HME or HME material.

Adjustable HMEs in Use

Figure 16:
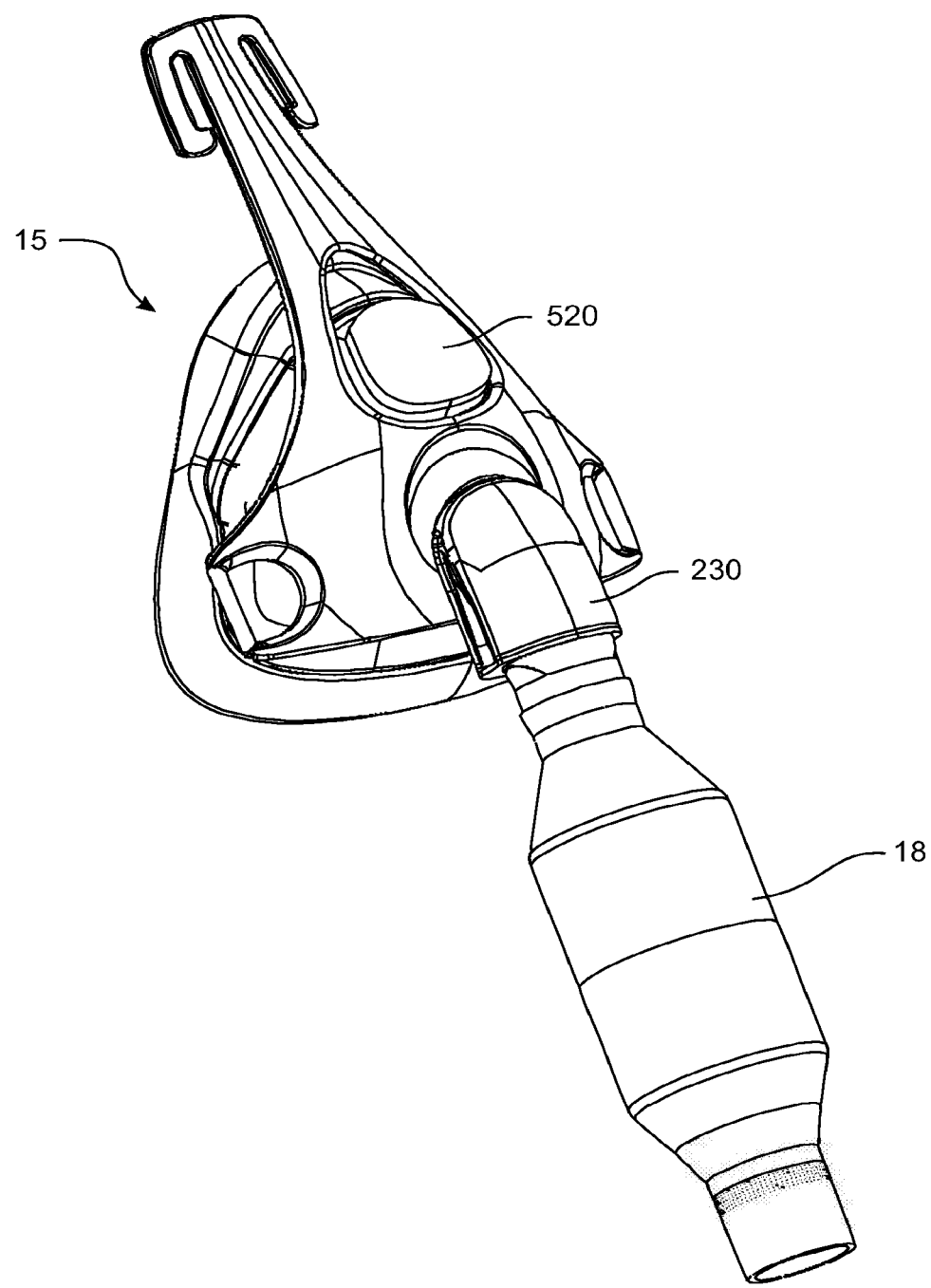
FIG. 16 shows a perspective assembled view of a patient interface and an adjustable HME.

Referring to FIG. 16. Adjustable HMEs 18 according to the above configurations may be connected between a patient interface 15 and a blower 11 or flow generator. In one arrangement, the adjustable HME 18 is coupled directly on one end to a patient interface 15, such as a mask or cannula (or through a connecting elbow 230), and coupled on the other end to a blower 11 or a conduit 14 for delivering flow to a patient. The adjustable HME 18 will function according to embodiments above and provide humidification to the patient.

Figure 17A:
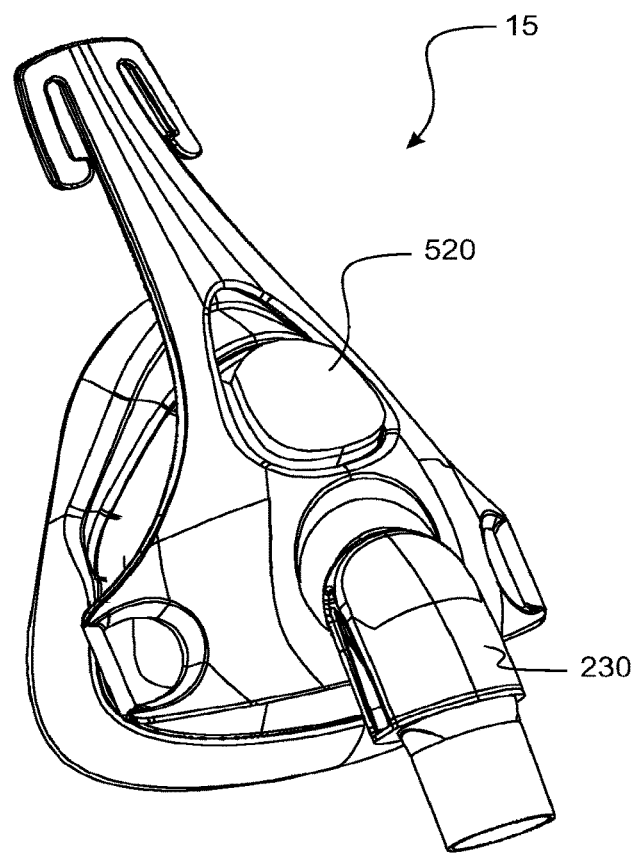
FIGS. 17a to 17c shows perspective and exploded views of a ventilation cap for a patient interface.
Figure 17B:
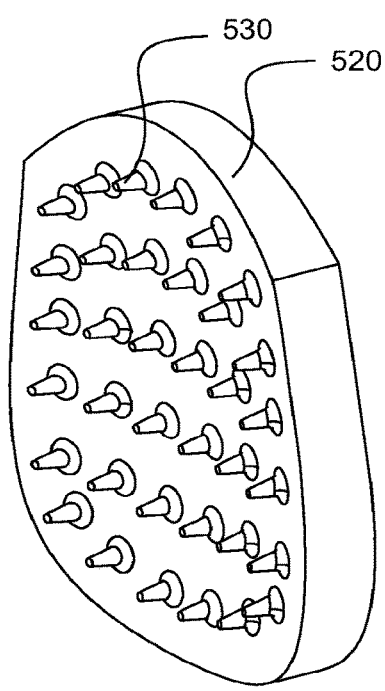
Figure 17C:
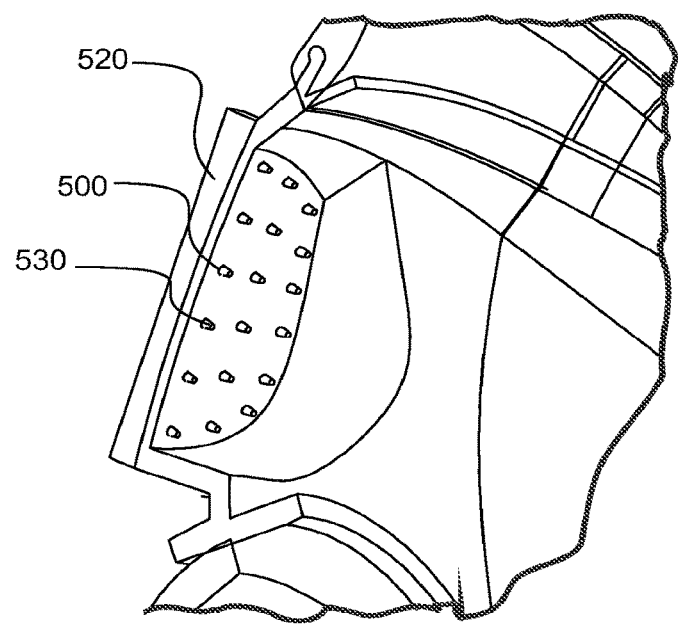
Figure 18A:
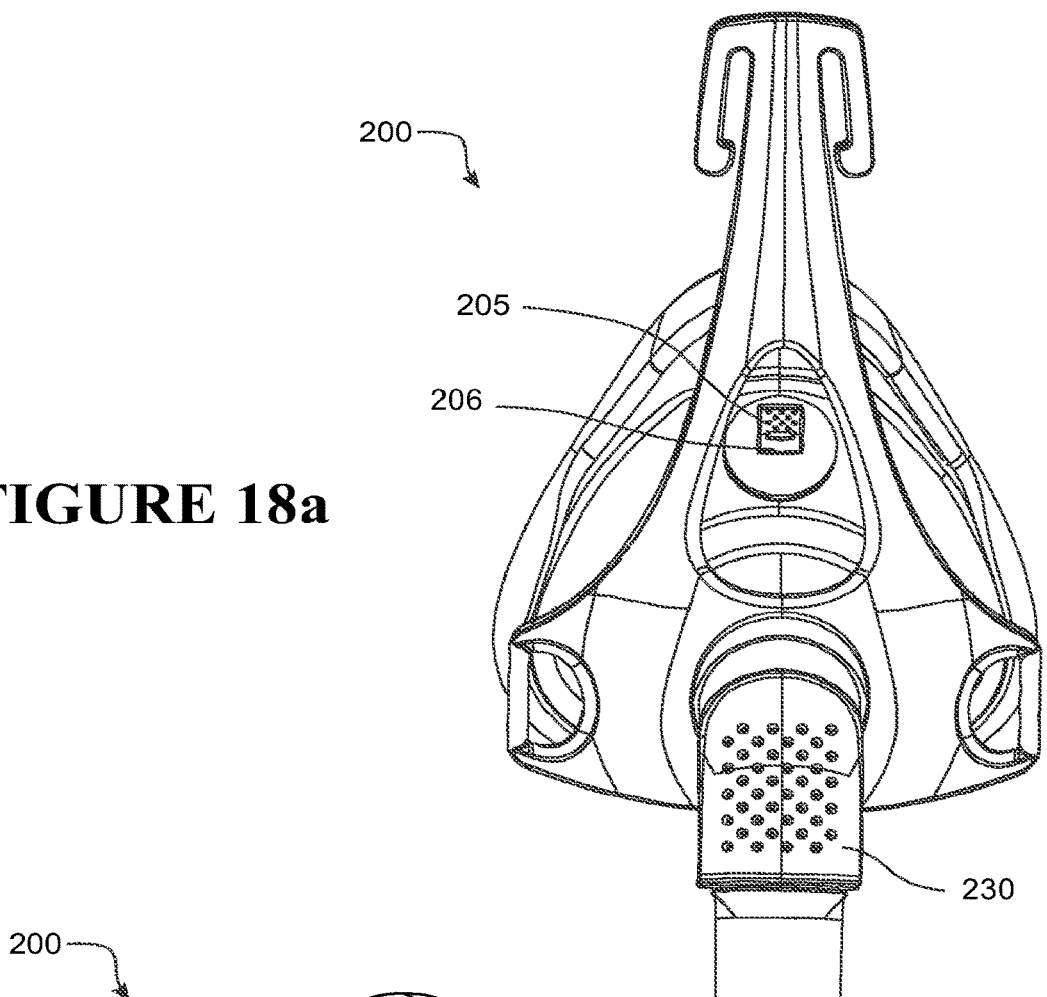
FIGS. 18a to 18d shows perspective and sectional views of an adjustable HME integrated into a patient interface.
Figure 18B:
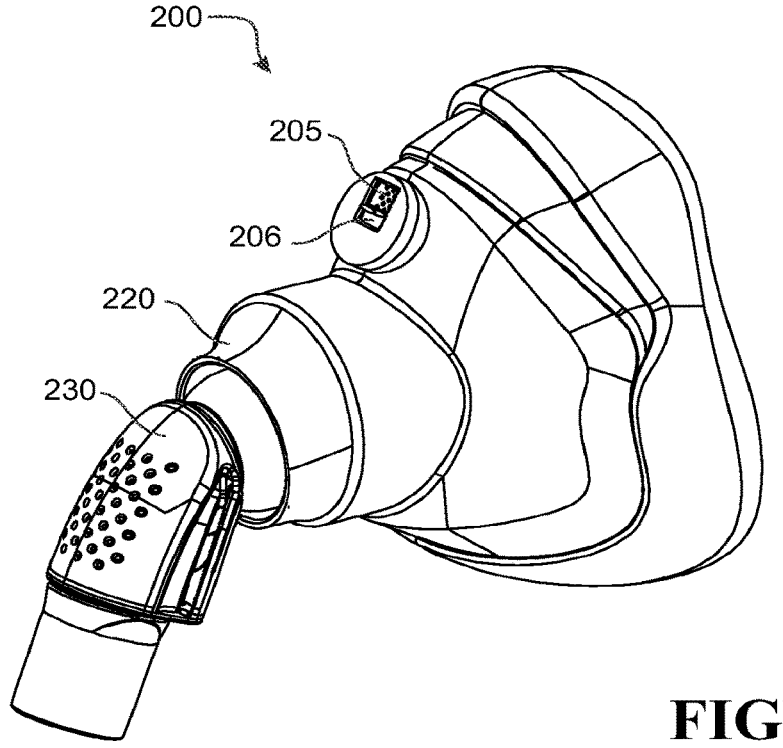
Figure 18C:
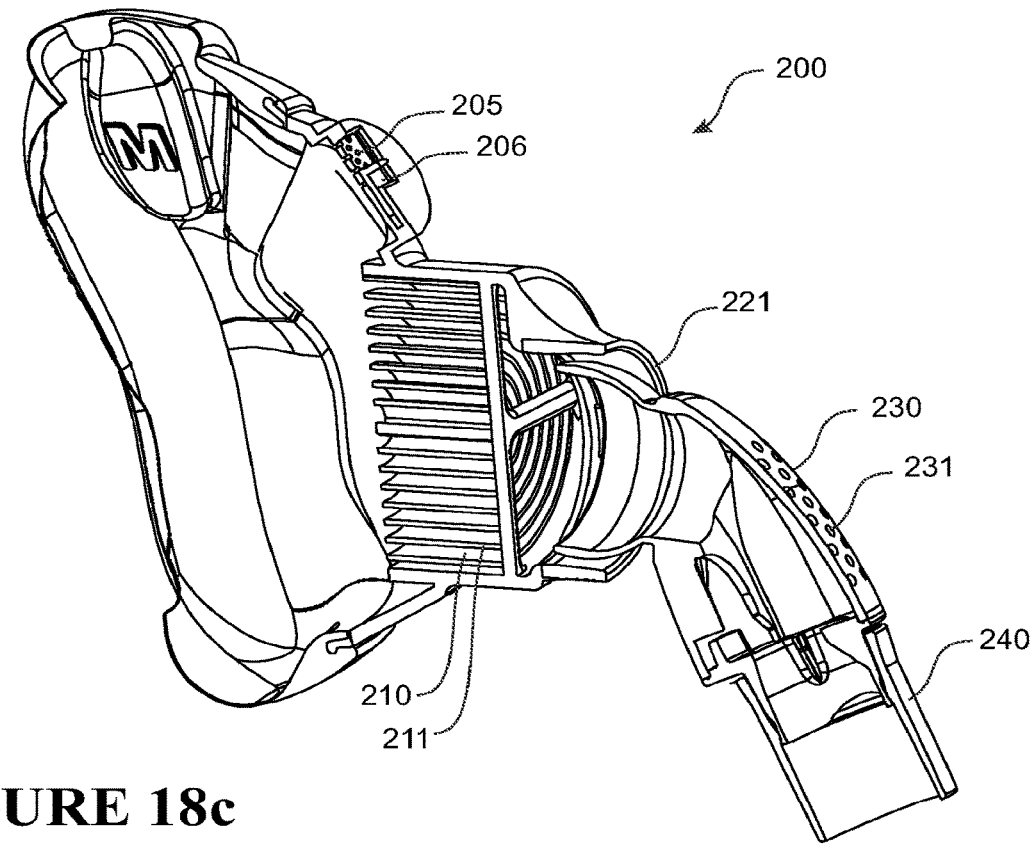
Figure 18D:
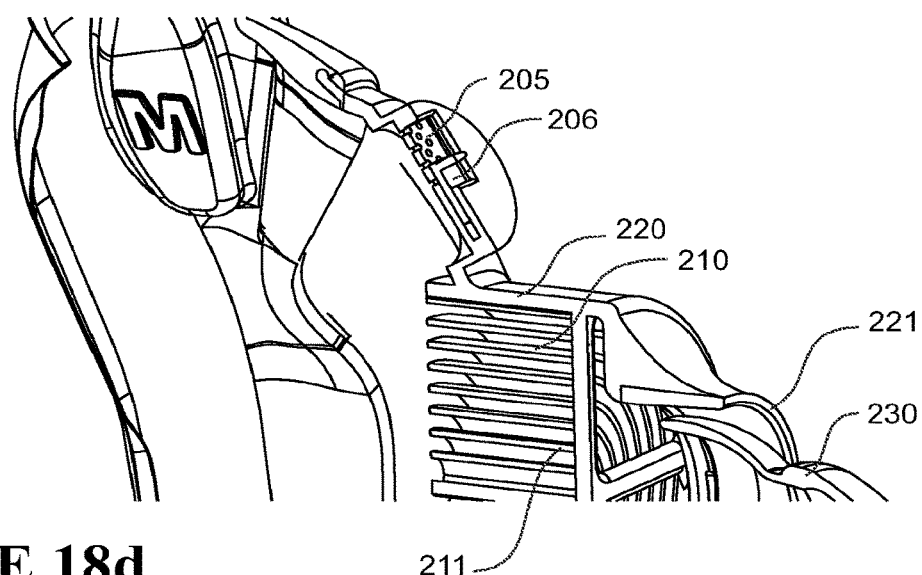

A number of commercially available patient interfaces 15 on the market today also provide ventilation holes either on the interfaces 15 or on the elbows 230. Such ventilation holes provide exit outlet for carbon dioxide and exhale patient air flow to ambient. However such ventilation holes would interfere with the working of the adjustable HMEs 18 as described above and with the bias flow holes 31 already built into the adjustable HMEs 18. Referring to FIGS. 17a to 17c, a ventilation cap 520 may be provided to seal off any existing ventilation holes on patient interfaces 15 such that the patient interface 15 can be used with the adjustable HMEs 18 as described. The ventilation cap 520 comprises protrusions 530 which can be plugged into the ventilation holes, effectively sealing holes such that all the patient air 30 flow is directly towards the adjustable HME 18 and the flow becomes regulated by the HME 18. The ventilation cap 520 may be made from rubber or any suitable material. The use of the ventilation cap 520 advantageously allows the adjustable HME 18 to be fitted or retrofitted to any suitable patient interface 15. Additionally, as discussed below with respect of FIG. 18a, the ventilation cap may include an adjuster 206 in the form of a movable slider/cover 206 may be used to open or close the ventilation outlets 205, which would allow for adjustment of humidity delivered and a patient can select how exhaled air is vented or biased.

New HME Materials

Figure 9:
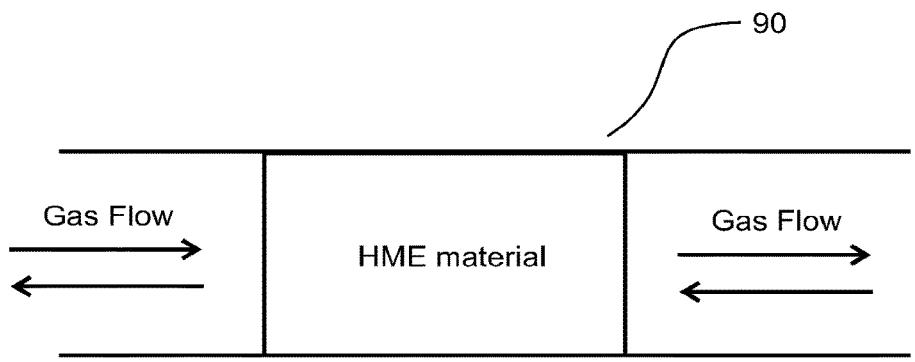
FIG. 9 shows a non-adjustable HME in schematic form.

New types of HME material could be used in an HME, beyond those known and used by those skilled in the art. The new HME materials described below could be used in any of the adjustable HME embodiments described above, or alternatively in non-adjustable HMEs 90, such as shown in FIG. 9. Preferably, a volume of about 12,000 mm$^3$ to 70,000 mm$^3$ of HME material is used.

Figure 10A:
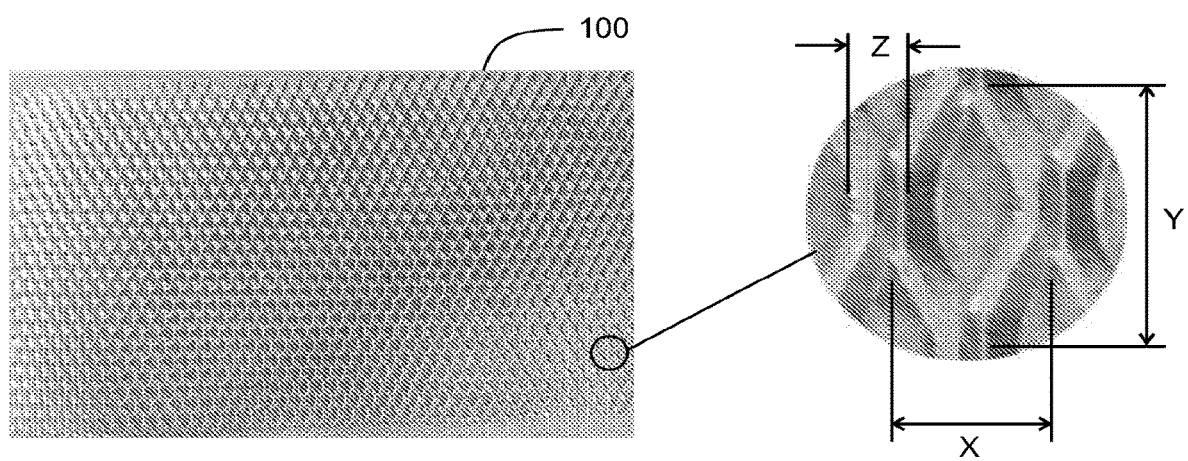
FIGS. 10a, 10b shown aluminium mesh in flat and spiral wound configurations.
Figure 10B:
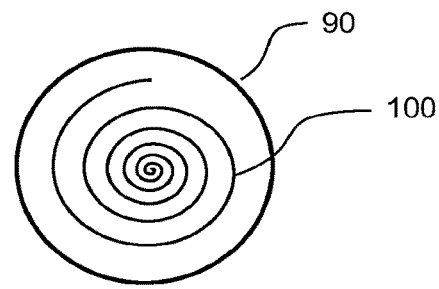

A first type of HME material that could be used is aluminium mesh/grille 100 or expanded sheet, such as shown in FIG. 10a. The aluminium mesh is light and flexible, and has a high surface area. This is suitable for retaining water from exhaled air and then releasing it during inhalation. The aluminium mesh 100 could be rolled up into a spiral or coil such as shown in FIG. 10b to fit in an adjustable or non-adjustable HME 90. The undulating nature of the mesh 100 means that when it is rolled up, there are plenty of gaps for gas flow to improve gas exchange (see also FIGS. 10c through 10h, discussed in detail below). The "diamonds" of the mesh also provide collection points for water condensation. Generally dimensions X, Y, Z of the diamonds can vary widely, however, as discussed below, the raised surface of the material provides benefits in forming tortuous air paths for the inlet and exhaled air to flow.

The aluminium mesh can be washed, sterilised or otherwise cleaned to reduce containments and bacteria without losing performance. Aluminium also allows for rapid cooling and heating to keep the material at the dew point to improve efficiency of humidity transfer. These effects are important as known HME materials, such as foams, are rather delicate, thus are difficult to handle or clean without damage.

Alternatively, a copper mesh could be used, or a mesh of any other suitable metal with suitable heat conduction/retention properties. The aluminium/copper/metal mesh can be produced by a process of expanded metal meshes with a "raised surface". For expanded metal, preferably between 15,000 mm$^2$ and 780,000 mm$^2$ of sheet metal is used. Preferably 33,000 mm$^2$ and 132,000 mm$^2$ of sheet metal is used. More preferably 75,000 mm$^2$ to 110,000 mm$^2$ of sheet metal used. The mesh has diamonds that have a width x and height y. The lattice of the mesh has thickness z. The diamond size, lattice thickness and number and density of diamonds can be configured to create the desired humidity transfer. The preferred dimension of the aluminium/copper/metal mesh is between 22 mm-120 mm in length, and 19 mm-60 mm in diameter. More preferably, the mesh dimension is between 40 mm-60 mm in length, and 40-50 mm in diameter. Even more preferably, the mesh dimension is 40 mm in length and 50 mm in diameter.

In addition to metals, polymer materials in mesh form having raised surfaces may also be used as the HME material. As such, the above description with respect to metal materials applies to polymers as well. In particular nylon, polypropylene, thermoplastic elastomers, and copolyester thermoplastic elastomers (for example as sold as Arnitel®, a water permeable polymer) may be used as the HME material as formed into mesh materials have a raised surface. Polymer materials provide for similar durability and cleaning benefits as described above with respect to metal mesh.

The HME material may also be arranged or stacked in series relative to each other. For example, coils of the aluminium or copper mesh could be stacked relative to each other in a series with respect to the flow path to increase surface area and improve water/moisture retaining capability.

Figure 10C:
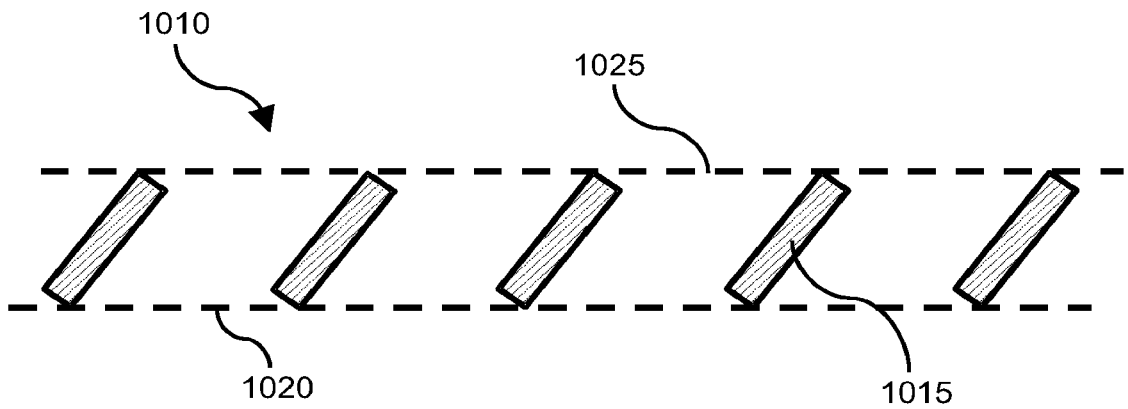
FIGS. 10c to 10e show cross sections of polymer and/or metal materials configured to have a "raised surface"
Figure 10D:
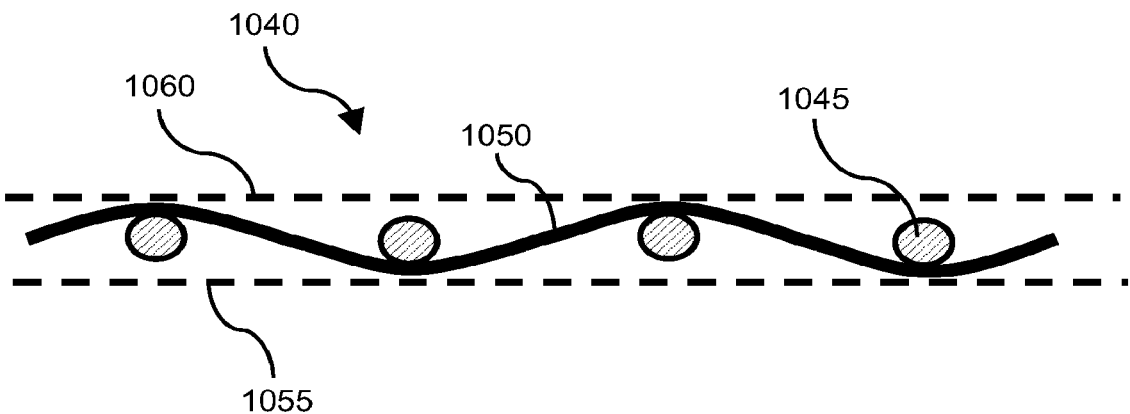
Figure 10E:
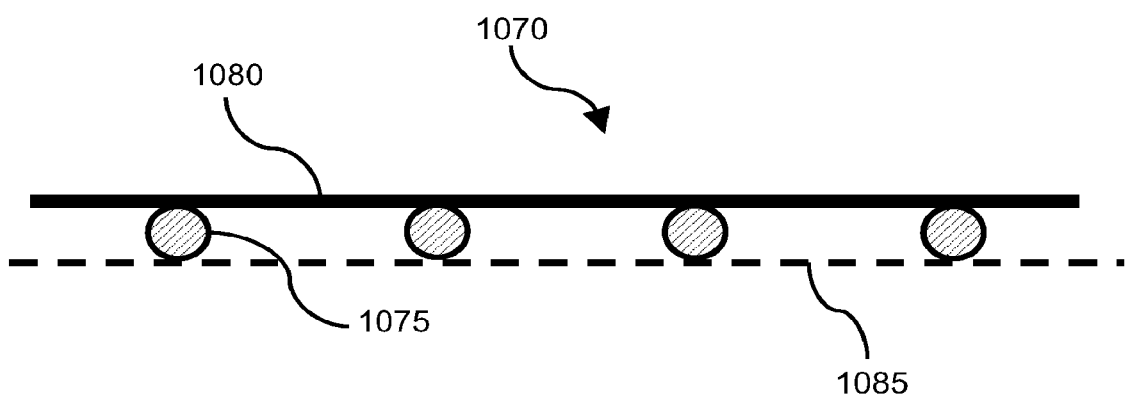

Shown in FIGS. 10c through 10e are non-limiting exemplary embodiments of the mesh materials having a raised surface described above, shown in cross-section. As shown in FIG. 10c, an expanded material 1010 is comprised of generally angle sections 1015. Dashed line 1020 represents a lower surface and dashed line 1025 represents a raised surface. The expanded material 1010 may be comprised a metal, polymer, and/or a metal covered polymer.

Shown in FIG. 10d is a non-limiting exemplary embodiment of the mesh material having a raised surface, shown in cross-section. As shown, a woven material 1040 is comprised of laterally aligned portions 1045. An interwoven portion 1050 is woven through the laterally aligned portions 1045. Dashed line 1055 represents a lower surface and dashed line 1060 represent an raised or upper surface.

Shown in FIG. 10e is a non-limiting exemplary embodiment of the mesh material having a raised surface, shown in cross-section. As shown, a lattice-type material 1070 is comprised of laterally aligned portions 1075 and a cross portion 1080 laid across the laterally aligned portions 1075. Dashed line 1085 represent a lower surface. In this embodiment, cross portion 1080 represents an upper surface.

Figure 10F:
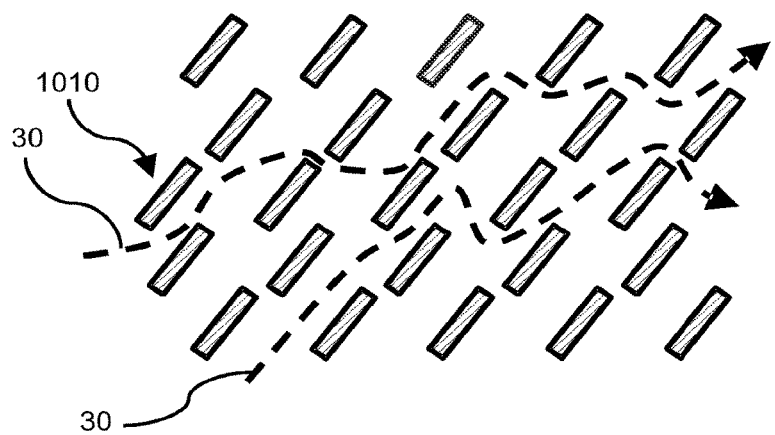
FIGS. 10f to 10h show the embodiments of polymer and/or metal materials coiled or layered or stacked to form flow paths or channels.
Figure 10G:
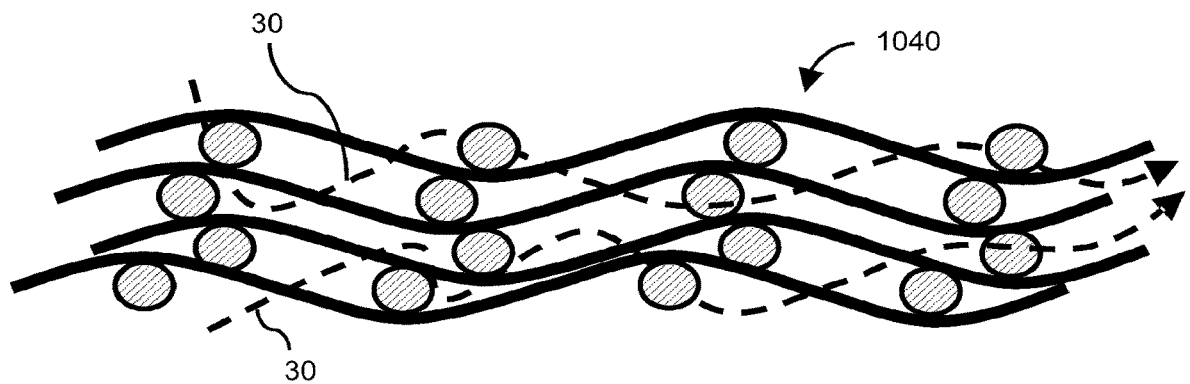
Figure 10H:
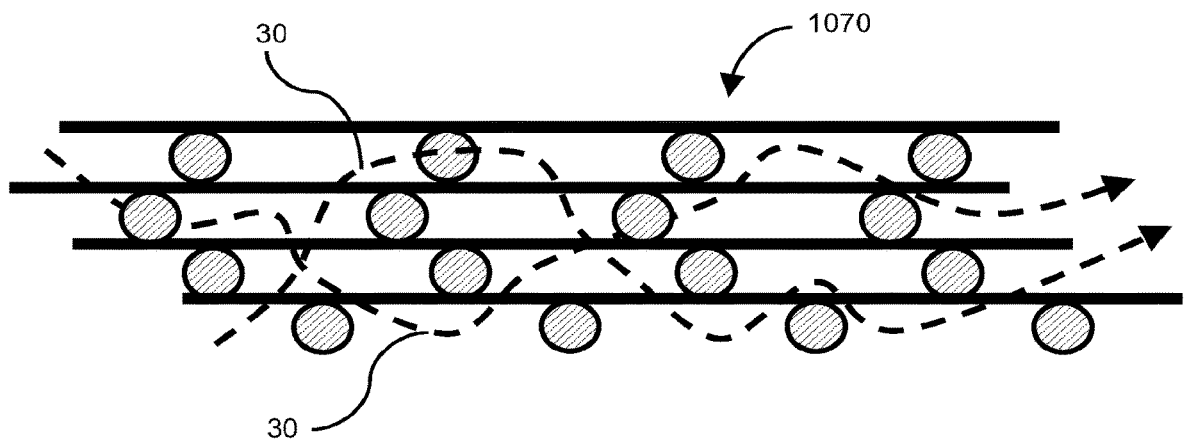

Shown in FIGS. 10f though 10h non-limiting exemplary embodiments of mesh materials having a raised surface in stacked, coiled, wound, or layered configurations. As shown, when stacked, coiled, wound, or layered, a plurality of various air paths are created, thus increased the volume and surfaces area of material for heat, moisture and/or humidity to be deposited. Exemplary air paths 30 are shown. Further, the mesh materials with raised portions may or may not be stacked in any particular order, thus forming either uniform or non-uniform flow paths. In particular, where the mesh material with raised surface is coiled, the decreasing radius of the coil will cause the raised surfaces to be aligned in different configurations throughout the coil, thus forming air paths of different shapes and/or sizes.

An alternative HME material could be a plastic mesh with a metal coating, such as aluminium or copper. This would be thinner and lighter and would allow for more HME material to be packed in an HME, thus improving volume of water transfer in and out of the gas flow. Another alternative HME material could be a plastic mesh coated with either hydrophilic or hydrophobic materials.

Figure 11:
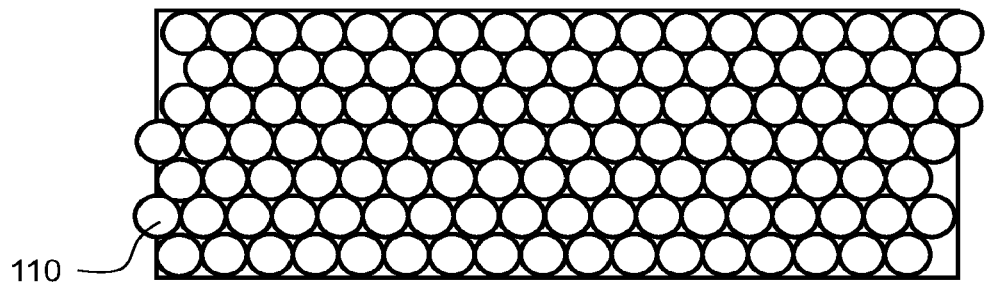
FIG. 11 shows Zeolite in an HME in schematic form.

An alternative HME material is a molecular sieve such as zeolite granules (particles) 110 as shown in FIG. 11. These are porous and have a high surface area providing high humidity transfer per gram of material. Water collects on the surface and pores of the granules 110 during exhalation, and is transferred back to the gas flow during inhalation. Zeolite can be easily washed, sterilised or otherwise cleaned without losing performance. Alternatively, synthetic zeolite can be used. In more general terms, any molecular sieve could be used. A molecular sieve can have a uniform and define pore size. One example is a molecular sieve type 3A (as in 3 angstrom pore sizes) made of alkali metal alumina-silicate. In any of the molecular sieve embodiments, preferably between 8 to 32 grams of material is used.

Another alternative HME material could be nano-fibre. Such nano-fibre material could be made using polyelectrolyte polymer (PSS), also known as polysalts, having hygroscopic characteristics similar to electrolytes. The polyelectrolyte polymer can be combined with another material to create structure. For example, an HME material can be made by blending polyamide66 (PA66) and polyelectrolyte polymer into an electrospun nano-fibre material. This material would behave similarly to materials impregnated with calcium chloride salts (per HME known in the art), with the further advantage of preventing loss or dissolution of polyelectrolyte polymer when washed. Therefore such nano-fibre material can be cleaned and re-used without losing its hygroscopic properties.

A further alternative HME material may comprise polymer materials including nylon, polypropylene, thermoplastic elastomers, and copolyester thermoplastic elastomers (for example as sold as Arnitel®, a water permeable polymer). Suitable polymer materials may be processed according to any of the above arrangements similar to aluminium/copper/metal mesh, such as coiled up in a mesh or netting that include a raised surface. The polymer materials may also be arranged or stacked in a series relative to each other (see e.g., FIGS. 10f to 10h).

Figure 12A:
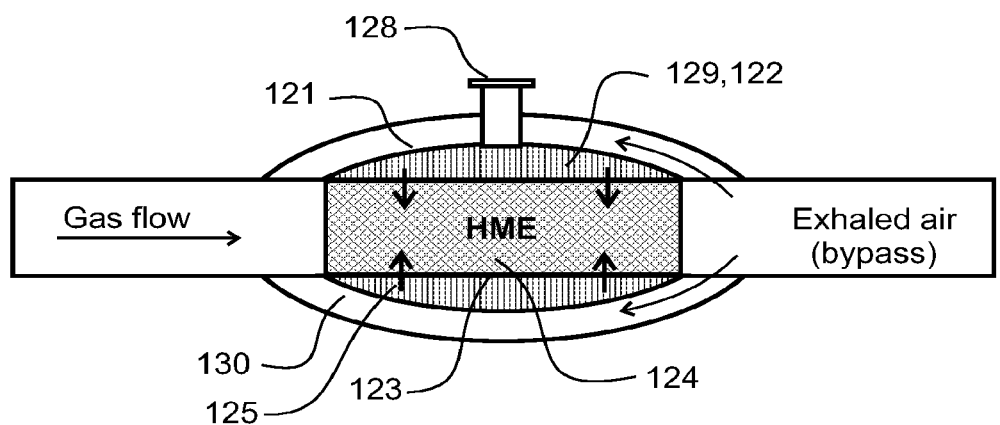
FIGS. 12a, 12b show an HME with a water chamber.
Figure 12B:
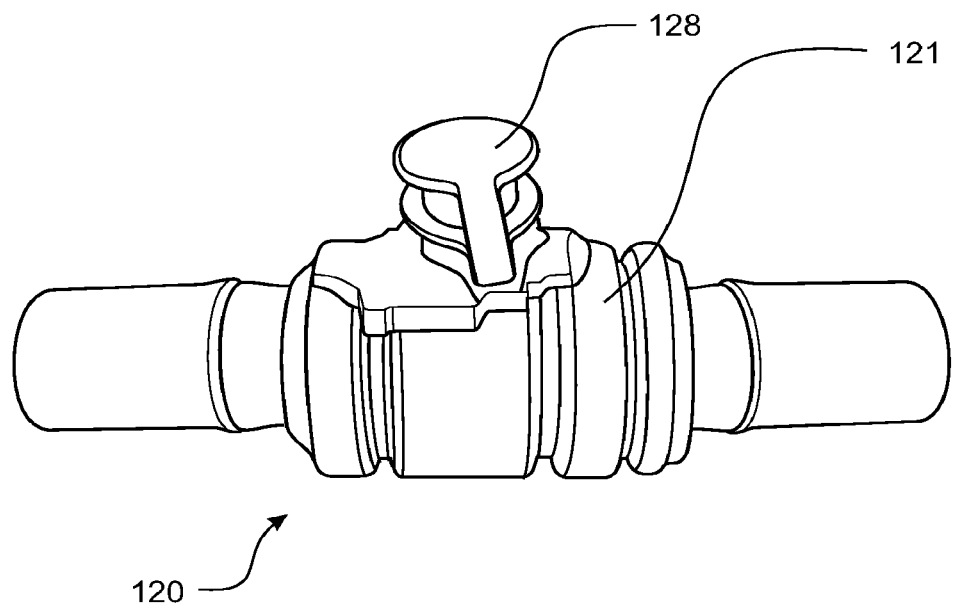

Even when using an HME there is not 100% efficiency in recycling humidity, not all water is captured and/or transferred back to the inhalation gas flow. In a further embodiment, a supply of water is provided to the HME to replace water that escapes from the HME or other parts of the breathing system. The supply of water is provided in a chamber 121 that is provided to an adjustable or non-adjustable HME 120. An embodiment shown comprising an adjustable HME is shown in FIGS. 12a, 12b. The water chamber comprises a housing surrounding the HME with a closable opening 128 for introducing water 122 into the chamber. The chamber comprises an internal region for storing water, or for housing a sponge 129 or other porous material that will retain water. A wall 123 (see FIG. 12b) with openings or made with porous material is disposed between the chamber 121 and the HME material 124. Alternatively, a water breathable membrane could be used for the wall 123, or any other water permeable material or construction. Water from the chamber is drawn 125 into the HME material through the wall 123 from the chamber 121 as humidity is lost from the system. A bypass channel 130 is provided around the chamber for passage of by-pass exhaled air. The channel has an adjustable mechanism, for example any of those disclosed previously, for controlling volume of by-pass air to control the humidity transferred to inhaled air. Any of the HME materials described (including traditional HME materials) could be used in this embodiment.

Incorporating HMEs into Patient Interface

As described above, an HME can be included in the patient interface itself, rather than between the patient interface and/or conduit and/or CPAP apparatus.

HME Integrated into Patient Interface

In one embodiment, rather than coupling the HME 18 between a patient interface 15 and a flow generator, the HME 18 can instead be integrated directly into a patient interface 15. Integrated HME 18 into a patient interface 15 advantageously provides a compact form so that it is easier for patients to use, requiring no separate HME parts. It is also discovered that integrating HME 18 into the patient interface 15 is a solution to the problem of carbon dioxide ($CO_2$) build-up inside the patient interface when used with an adjustable or non-adjustable HME. The HME 18 to be integrated may comprise any embodiments of adjustable HMEs herein described, or a standard non-adjustable HME.

FIGS. 18a to 18d show perspective and sectional views of a patient interface 200 with a HME 210 integrated. The HME could be any described herein. The patient interface 200 could be any interface, mask or cannula suitable for delivering air to a patient. The patient interface 200 may work with a breathing apparatus, such as (and without limitation) a CPAP, bi-level, autotitration or NIV apparatus. The patient interface 200 may be coupled to an elbow 230 or a conduit 240 which is fluidly connected to an outlet of a breathing apparatus. The HME material 211 may comprise any suitable material described herein. In one embodiment, the HME material is aluminium/copper/metal mesh. In another embodiment, the HME material is polymer, polypropylene or nylon.

The patient interface 200 comprises an inlet 221 for receiving air from a breathing apparatus; the inlet 221 is fluidly connected with an elbow 230 or a conduit 240. A chamber 220 is defined between the inlet 221 and the interior of the patient interface to house the HME 210. An HME adjuster (not shown) substantially as described above manipulates the HME material 211 to adjust the surface area exposed on the HME material 211 and hence the amount of humidity exchanged. In use, airflow passes from the conduit 240 and/or the elbow 230 into the chamber 220 through the HME material 211, picking up any humidity from the HME 210, and inhaled by the patient. Exhaled air from the patient passes through the HME material 211 and deposits water/moisture on the material. The exhaled air from the patient passes the HME material 211 and deposits humidity onto the material. Exhaled air from the patient may also exit to ambient through ventilation outlets 205 on the patient interface or bias flow holes 231 on the HME 210 (not shown) or elbow 230. In one embodiment, an adjuster 206 in the form of a movable slider/cover 206 may be used to open or close the ventilation outlets 205, and hence amount of airflow to ambient through such outlets 205. It may be desirable to stop or reduce airflow to ambient via the ventilation outlets 205 on the patient interface 200 such that exhaled airflow primarily passes through the HME material 211 and deposit humidity onto the HME material 211. The airflow subsequently exits through the bias holes 231 either on the HME or the elbow 230. However it may be necessary to adjust the ventilation outlets 205 on the patient interface 200 to reduce $CO_2$ build-up inside the patient interface 200.

FIGS. 19a to 19e illustrate multiple configurations of ventilation outlets and adjusters on a patient interface 15. The patient interface 15 can be any interface such as mask or cannula suitable for delivering air to a patient. Depending on environment conditions such as ambient temperature and airflow pressure, excess carbon dioxide ($CO_2$), heat, and/or humidity may build up within the patient interface 15 when used with a HME. Adjustable ventilation outlets 500 and adjusters 510 may be incorporated into such a patient interface 15, creating additional airflow pathways that helps remove $CO_2$ build up, as well as allow for reduced heat moisture retained from the interface 15. As a result, less condensation or rainout is present in the patient interface.

In one embodiment, the ventilation outlets 500 are located adjacent nasal area of the patient interface, and comprise small ventilation holes. While the adjuster 510 is a slider which can be configured to open, partially cover, or fully cover the ventilation holes. In another embodiment, the ventilation outlet 500 is a vertical slit, slot or gap, and a slider may be used to open, partially cover or fully over the vertical slot or gap.

Figure 19A:
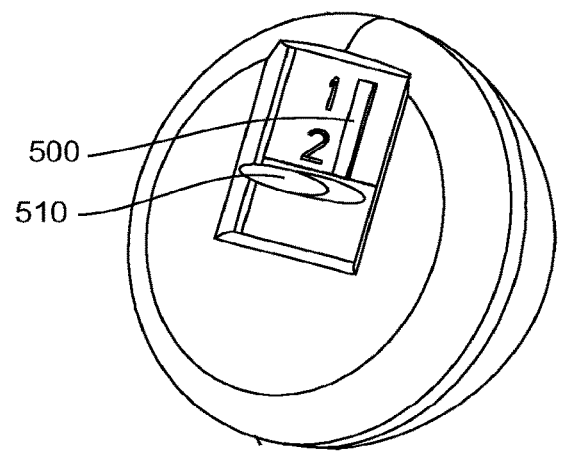
FIGS. 19a to 19e show examples of adjustable ventilation holes for patient interface.
Figure 19B:
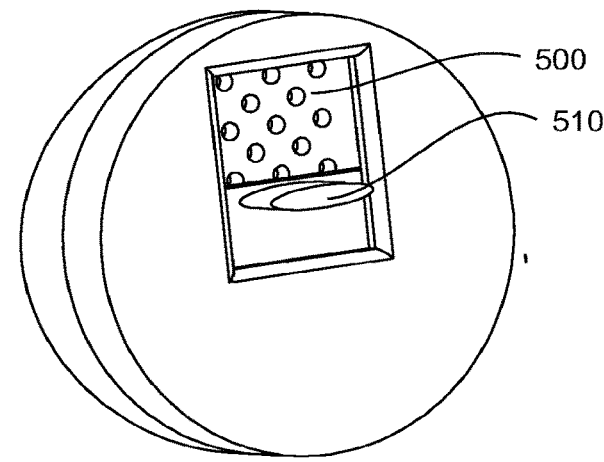
Figure 19C:
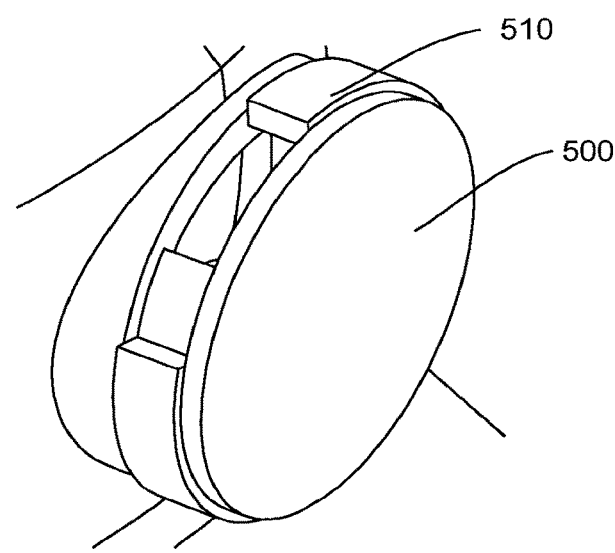
Figure 19D:
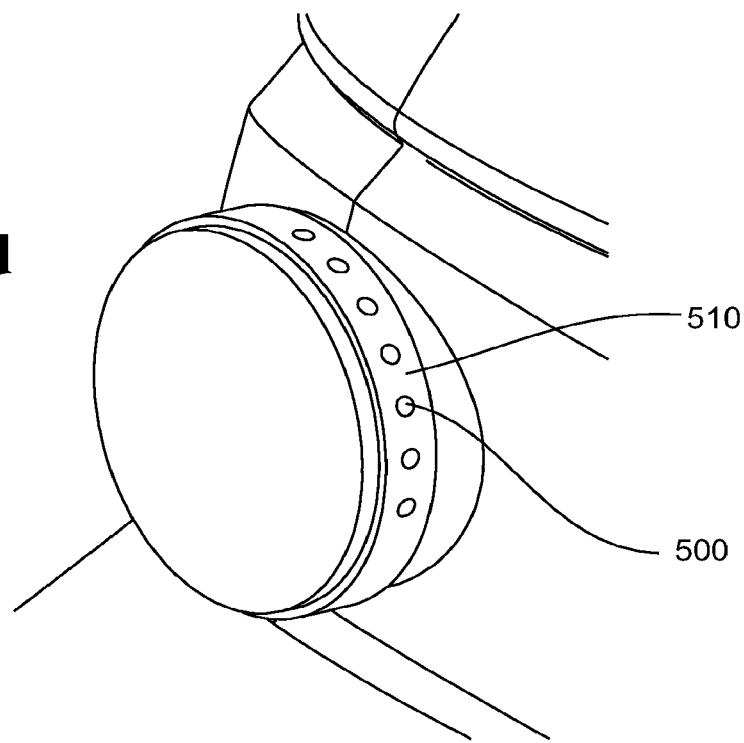
Figure 19E:
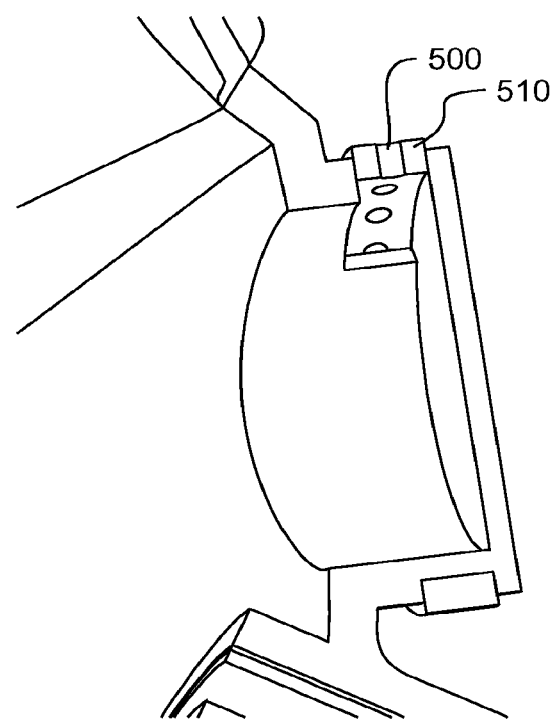
Figure 20A:
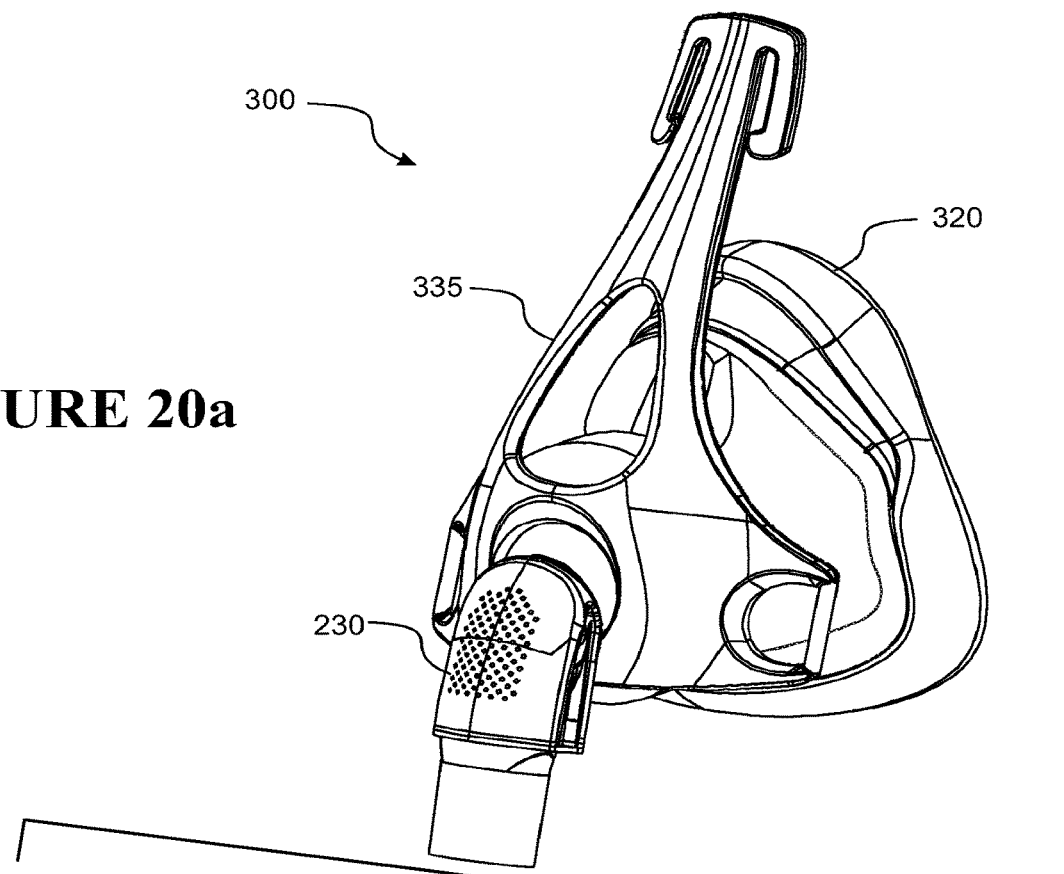
FIGS. 20a to 20d shows perspective, exploded and sectional views of an adjustable HME modularly integrated into a patient interface.
Figure 20B:
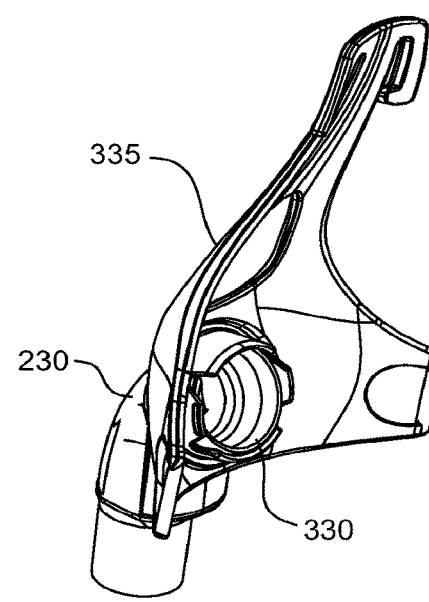
Figure 20C:
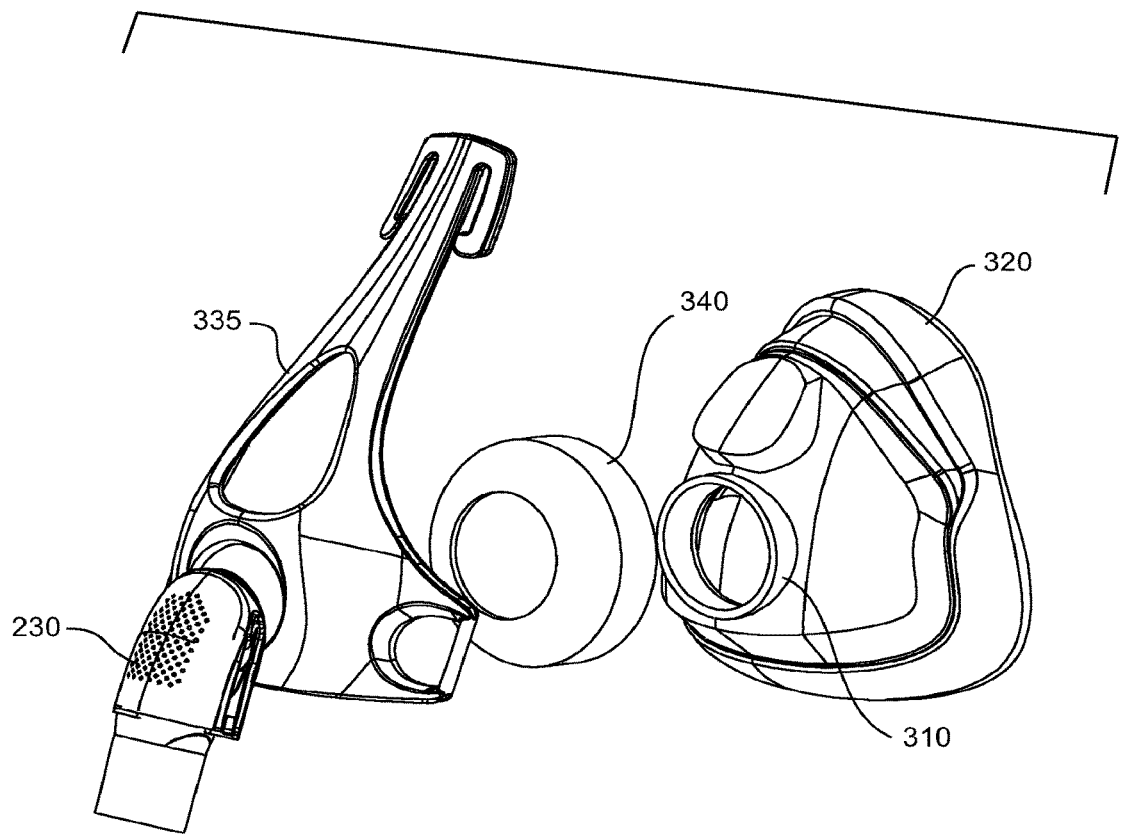
Figure 20D:
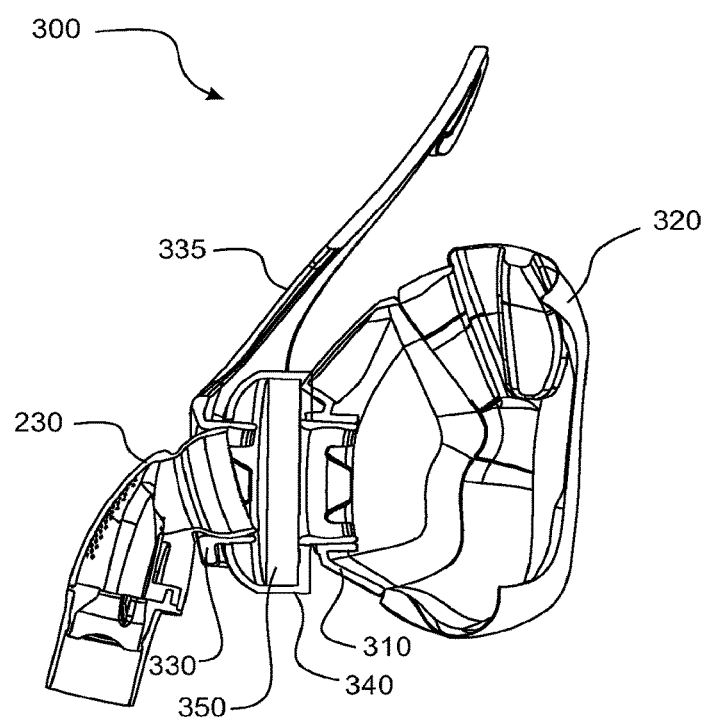

FIGS. 19c to 19e illustrates another embodiment of the ventilation outlets 500, where the ventilation outlets comprise a partially annular opening which can be adjustably covered by a ring 510 rotatable between open, partially open and closed positions. In another arrangement, the rotatable ring 510 comprises apertures partially along its perimeter, and the ring 510 (and apertures) is rotatable between open, partially open and closed positions, where the apertures aligns and misaligns with the ventilation outlets. It is discovered that this arrangement is likely to be quieter due to smaller aperture holes on the ring 510.

Additionally, different positions of the ventilation adjusters may be labelled corresponding to how much air is allowed to flow through the ventilation holes. Examples of labels may include numerals, alphabets or any other suitable labels to denote the relative degree of which the ventilation holes are open.

Modular HME for Connection to Patient Interface

FIGS. 20a to 20d shows an alternative modular HME embodiment that can be retrofitted to an existing patient interface. The patient interface 300 has three modular components; a patient contacting portion 320 (such as a cushion or seal) which comprises a connector 310, a modular HME in the form of a removable chamber 340 for housing a HME 350, and a conduit portion 330. The connector 310 of the patient contacting portion mask shell or housing 320 may be coupled to the conduit portion 330 to form a standard patient interface 300 without integrated HME capability. To enable HME capability, the removable chamber 340, which houses the HME 350, is coupled at one end to the connector 310 of the patient contacting portion mask shell or housing 320, and at another end to the conduit portion 330 in a mask frame 335. Once the removable chamber 340 is coupled to the patient interface 300, it can function like any of the adjustable or non-adjustable HME as described herein. The HME 350 may also comprise any suitable HME material as described herein. Patient interface 300 having a modular, removable chamber 340 allows the HME 350 to be easily accessed, cleaned or replaced/upgraded.

Figure 21A:
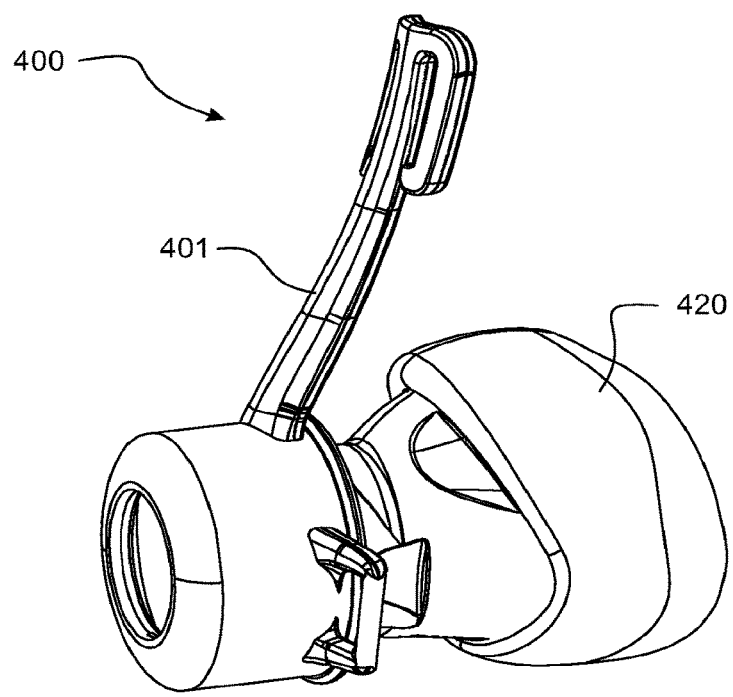
FIGS. 21a and 21b shows perspective views of another embodiment of an adjustable HME modularly integrated into a patient interface.
Figure 21B:
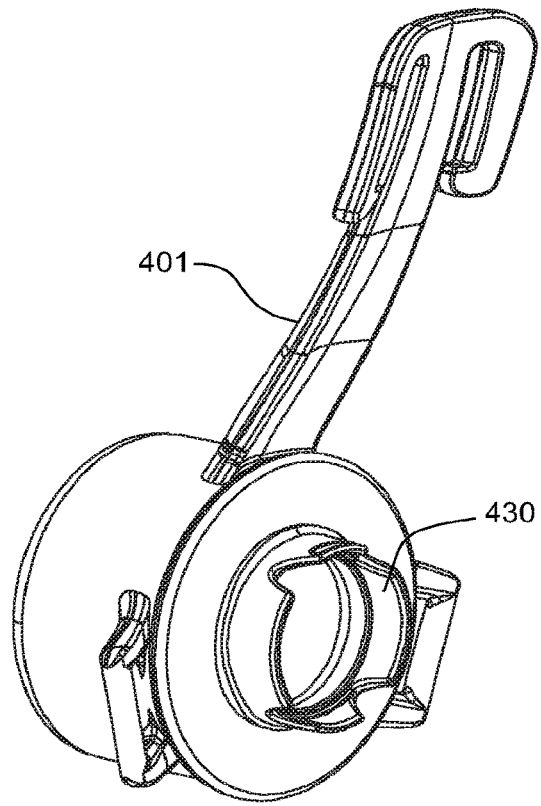
Figure 22:
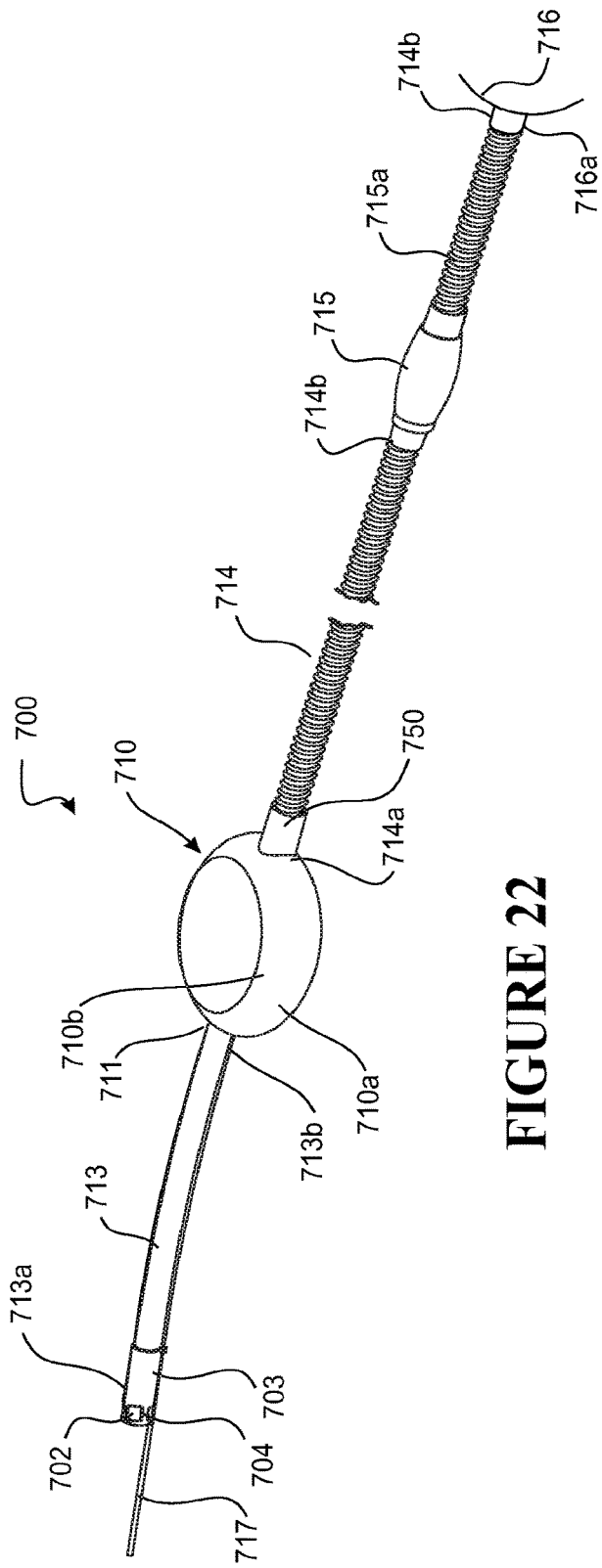
FIGS. 22 to 25 show, in schematic form, a compact breathing apparatus, in this case a CPAP apparatus, in solid and partially dismantled views.
Figure 23:
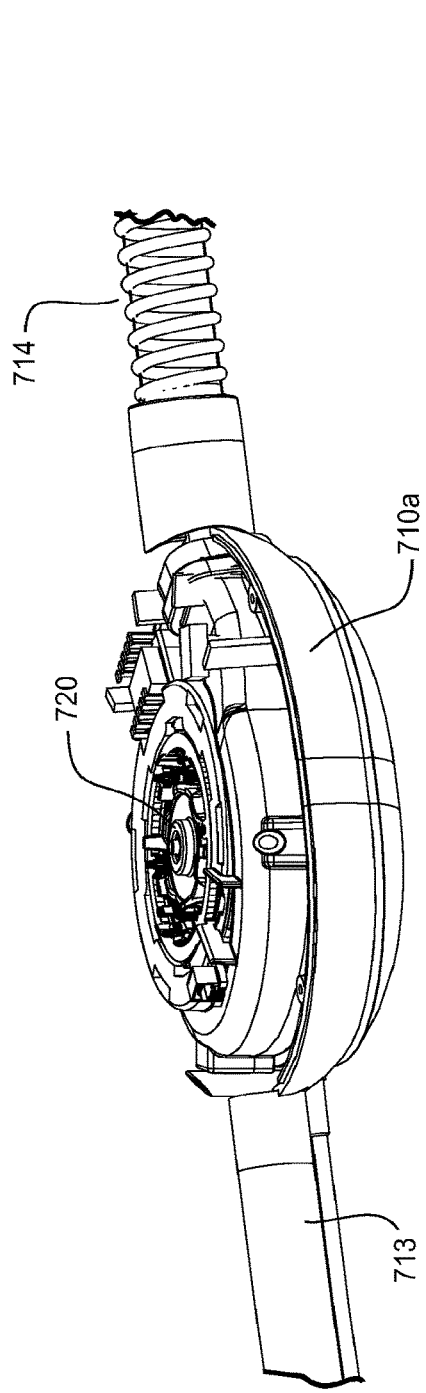

FIGS. 21a and 21b show another embodiment of modular HME. The patient interface 400 comprises a front portion 401 having a protrusion 430 which may be coupled to a patient contacting portion 420 or to a modular HME chamber.

Various modifications of integrated and modular HME for patient interfaces will be apparent to those skilled in the art without departing from the nature of the invention.

An adjustable ventilator for a patient interface as described above with reference to FIGS. 19a to 19e could also be used with a modular HME.

Compact CPAP

Breathing apparatus such as CPAP apparatus, non-invasive ventilators, bilevel, auto titration apparatus or the like provide therapy is that assists patient health.

Traditional apparatus are usually very bulky, and typically sit on a bedside table in a home environment. The bulk means that they are not easily portable, and also difficult to place in convenient locations—such as close to the patient. For example, a CPAP apparatus, which is typically used when a patient is asleep in bed, must be placed by the bedside table or similar. This is awkward when the patient is in bed and is not necessarily the best location for ease of use. When breathing apparatus become more difficult to use, often it means they are less likely to be used and patient compliance diminishes. Embodiments described here provide more convenient CPAP apparatus.

Overview of Apparatus

FIGS. 22 to 25 show an embodiment of a compact breathing apparatus 700, in this case a CPAP apparatus, although the invention is not restricted to such breathing apparatus. The breathing apparatus could also be a bilevel, autotitration, NIV or other breathing apparatus. The CPAP apparatus provides a pressurised air flow to a patient to treat obstructive sleep apnoea.

The breathing apparatus 700 comprises a main housing 710 for a blower/flow generator with a housing air inlet 711 for receiving ambient air and a housing air outlet 712 for providing pressurised air to a patient. A motor 720 (see FIGS. 23 and 24) is disposed inside the housing 710 with an output shaft 730 coupled to an impeller 731 (see FIG. 24) to form the blower. A flexible air inlet tube 713 is provided that has an ambient air inlet 713a at one end, and an outlet 713b at the other end that couples to the housing air inlet 711. The air inlet tube could have a replaceable filter element 702 in and terminating the flexible air inlet tube 713. The filter element 702 could have a housing 703 with openings 704 at the end and along the side, and optionally is in the shape of a cone. A patient breathing conduit 714 is provided that has a pressurised air inlet 714a at one end that is coupled (via a suitable coupling 750) to the housing outlet 712 for conveying pressurised air to a patient. Preferably, an HME (heat and moisture exchanger) 715 is provided for humidifying the pressurised air conveyed to the patient. The HME 715 is placed in the patient conduit 714 or connected to it, at some suitable position between the housing 710 and the patient interface 716. Preferably, and as shown in the drawings, the HME 715 is placed on the outlet end of the patient conduit 714/714b. It has an outlet conduit 715, with an outlet end 715a. The outlet end 715a is coupled to a patient interface 716 (such as a mask, cannula or the like) with a suitable coupling 716a such as elbow or swivel coupling. The breathing conduit 714 conveys pressurised air generated by the flow generator to the patient via the HME 715 and the patient interface 716. In an alternative, the HME 715 is placed between the housing 710 and the patient conduit inlet 714/714a, although this is less preferable. In another alternative, an HME 715 is not used and the patient conduit 714 is coupled directly to the patient interface 716 via coupling 716a. Where an HME 715 is used, preferably the patient interface 716 does not have exhaust vents (bias flow holes) as if it did, this would reduce the efficacy of the HME as the humidified air exhaled from the patient would pass to ambient before reaching the HME rather than passing back to the incoming air flow through the HME. Preferably, it is the HME 715 that has the exhaust vents on the flow generator side. Any of the HME described above or below could be used.

Upon operation of the motor 720, the impeller 731 rotates in the housing 710 and draws in ambient air through the flexible air inlet tube 713, pressurises it and directs the pressurised air out the outlet 712 through the patient conduit 714, optionally but preferably through the HME 715 where it is humidified, and to the patient via the patient interface 716.

The term "compact breathing apparatus" 700 can refer to the housing 710 and its internal components only, or alternatively also to the housing 710 in combination with one or more peripheral devices (such as although not limited to the air inlet tube 713, the patient conduit 714, the HME 715, the patient interface 716 and the like).

Components of the compact breathing apparatus will now be described in further detail.

Housing

The housing 710 comprises preferably two shell halves (710a seen in FIG. 23) that abut together to create an oval shaped housing with an internal region. The housing preferably has a low profile round exterior with no edges. A flexible e.g. silicon or rubber outer ring 740 (see FIG. 25) is preferably assembled over the abutment of the two halves 710a, 710b to create a soft feel and to cover the join line. The housing is preferably made from a sound damping material, such as long chain polypropylene.

Figure 24:
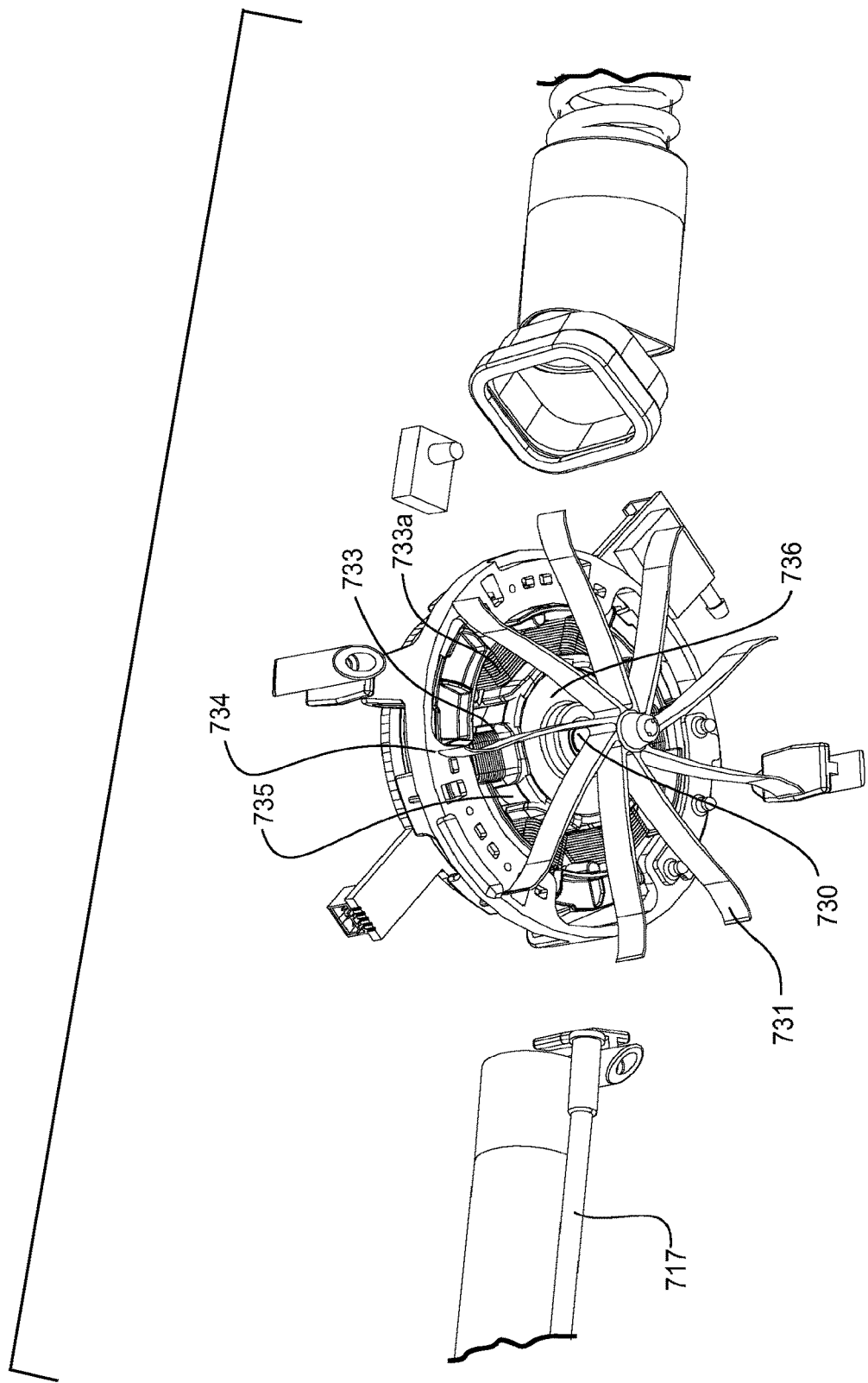
Figure 25:
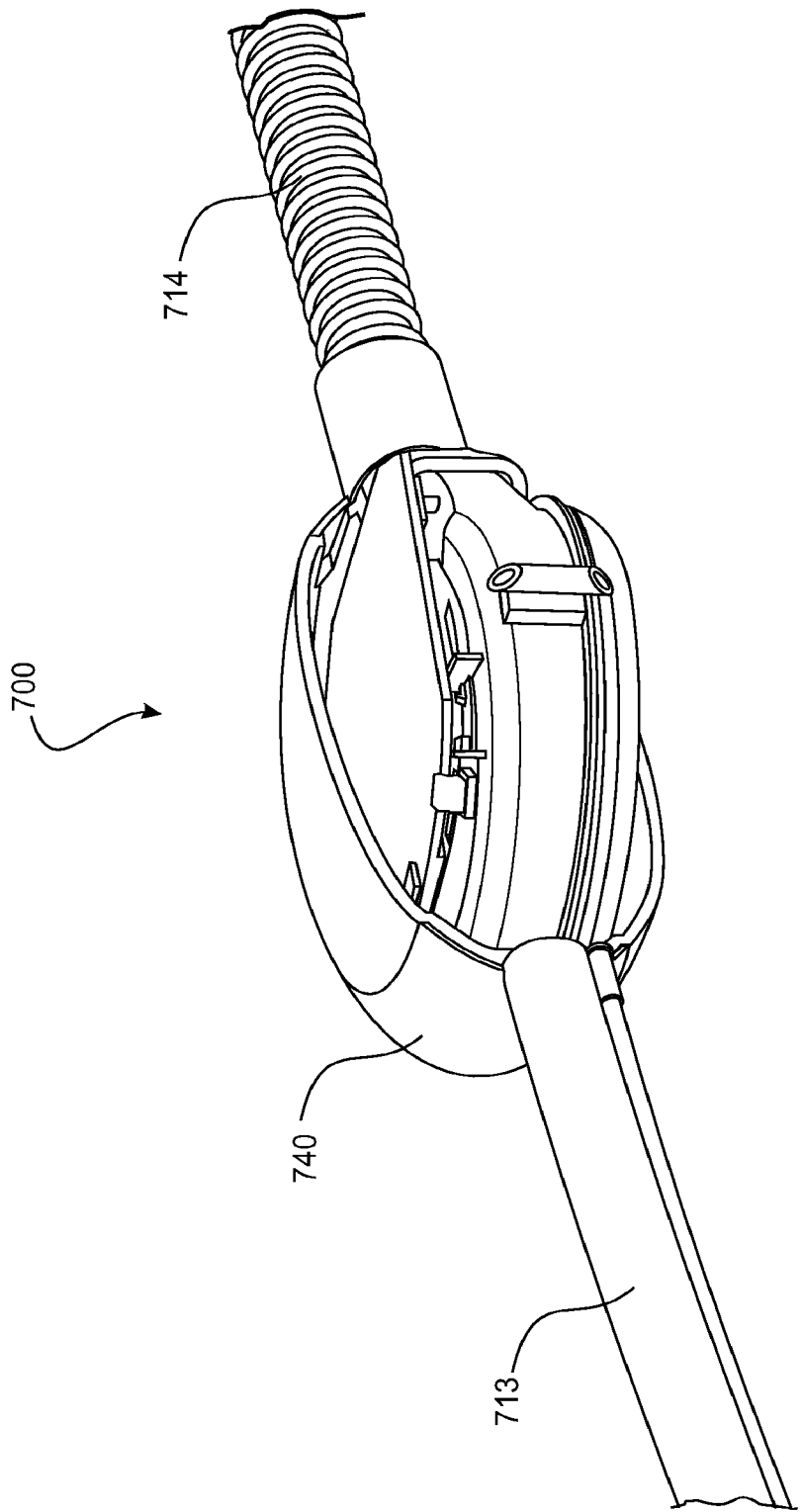

Referring to FIG. 24, preferably the motor 720 and impeller 731 are a low inertia motor/impeller assembly such as described in PCT/NZ2012/000124 published as WO2013/009193 (which is incorporated herein by reference in its entirety), although any suitable motor and impeller assembly could be used. The motor and impeller from PCT/NZ2012/000124 will be briefly described with reference to FIG. 24. The assembly comprises a stator with stator poles e.g. 733 supporting windings e.g. 733a. The stator is supported between two parts forming a stator frame. The stator frame has extensions aligned with each stator. A rotor 735 is disposed inside the stator between the stator poles and is connected to the impellers 731 by the shaft 730. The impeller/rotor assembly is positioned/aligned in the stator by way of resilient mounts 736 that are coupled to the stator frame extensions. The motor/impeller assembly is held in the housing 710 by a frame 734. It will be appreciated that any suitable motor can be used and low inertia impeller as described above is not essential.

The CPAP apparatus preferably has a power source comprising a plug pack that connects to a wall socket. A power cable is permanently fixed to the housing 710 to prevent inadvertent disconnection and prevent a non-approved plug pack from being used. Alternatively an external or internal chargeable battery could be used, optionally chargeable using inductive power transfer. Other power sources could also be envisaged by those skilled in the art.

Air Inlet Tube

The flexible air inlet tube 713 is provided to reduce the chance that the air inlet to the breathing apparatus 700 is occluded when the breathing apparatus is placed in a convenient location. This is particularly a problem that could be faced by the present compact breathing apparatus 700, as it may be used in places other than a bedside table or other traditional locations—rather it may be used on or In a bed or similar. The risk is that when used in such convenient locations, the air inlet 713a could become occluded and prevent the breathing apparatus 700 from operating correctly, or worse create a danger to the patient. The flexible air inlet tube 713 is made of a flexible material such as silicone rubber or the like so that it can be manipulated (by for example bending, stretching, twisting or the like) into a range of different geometric configurations to (during use) place the air inlet tube 713 so that air inlet 713a is in a position so it is free from occlusion. Preferably, the air inlet tube 713 also has an internal diameter wall ratio of 3:1 so that upon manipulation and/or external forces the tube 713 wall will not collapse, thus avoiding occlusion. However, other ratios are possible. For example, the tube could have a wall diameter in the range of 2.5 mm to 6 mm and a total diameter in the range of 16 mm to 20 mm. The length of the tube is preferably short, for example somewhere between 150 mm-300 mm. Preferably additionally, not only is the air inlet tube 713 flexible, but it is also malleable so it is easily retained/maintained in the chosen geometric configuration that it has been manipulated into, but then also easily reconfigured into another geometric configuration as required. To create a malleable air inlet tube 713, either the tube 713 itself can be made from a malleable material and/or it can comprise one or more malleable reinforcement elements 717. The malleable material that the air inlet tube 713 can be made from could be one or more of: ductile metal insert of steel or aluminium, deformable plastic or polyester or liquid crystal polymer, separate plastic links that can swivel inside each other, concertina deformable tube, or the like.

The malleable reinforcement element 717 can be an insert (such as a bendable wire or the like) that takes the form of a spine 717 that runs internally or externally to the air inlet tube 713. Manipulating the tube 713 into the chosen geometric configuration will also manipulate the spine 717 due to its malleability, and due to its retention properties will retain the tube 713 in the chosen geometry (in addition to any retention properties of the tube 713 material itself). Manipulation of the air inlet tube 713 will be described further below with reference to use of the breathing apparatus in relation to FIG. 27.

Patient Conduit

Figure 26:
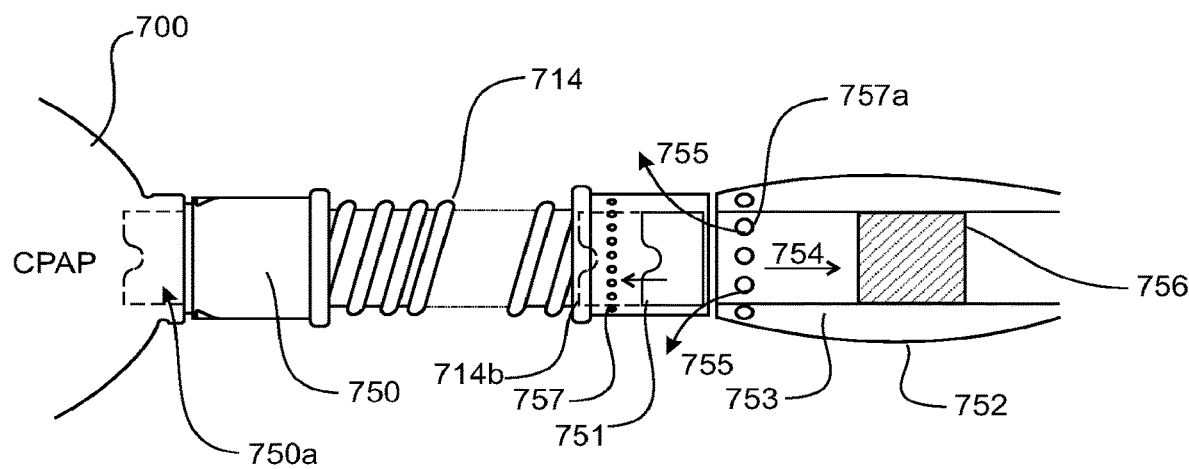
FIG. 26 shows an HME and its connection in the compact breathing apparatus.

Referring to FIG. 26, the patient conduit 714 could be any suitable conduit known to those skilled in the art the breathing apparatus, and could be a heated or non-heated conduit. The flow generator end 712/714a of the conduit preferably comprises a clip or a swivel connector 750 with a short spigot 750a to couple into a preferably female connection on the housing air outlet 712. The patient end of the conduit has a connector 716a for direct connection to the patient interface, or a connector 751 for a connection to an HME 715 (in which case the HME has an outlet tube 715a with coupling 716a for the patient interface). The patient end connector 751 has exhaust vents 757 as a precaution. In a preferred embodiment, the patient interface does not have exhaust vents as it is designed for use with an HME 715 with the exhaust vents. This means if the patient interface 716 is directly connected to the patient conduit 714 without an HME 715, there will be no exhaust vents unless they are provided within the patient conduit also. This would pose a significant danger.

Heat and Moisture Exchanger

In the preferred embodiment, an HME 715 is coupled to the patient end connector 714b of the patient conduit 714. A standard or adjustable HME 715 could be provided. The HME can take many forms. In one example, as shown in FIG. 26, it comprises a curved tubular housing 752 with a flow path 753 through it for inlet airflow 754 and patient expiration airflow 755. An HME material 756 is in the flow path and transfers humidity from the patient expiration airflow 755 to the inlet airflow 754 in a manner known to those skilled in the art. As mentioned previously, bias flow holes 757a are provided at the patient conduit end 714b of the HME 715 to allow for flow of patient expiration airflow 755. The HME 715 comprises a connector 751 that couples to the conduit connector 714b, and in doing so covers the conduit bias flow holes 757 in that connector when fully connected (see dotted lines). The bias flow holes 757 in the patient conduit connector 714b are not required when an HME 715 is being used, as the HME provides a bias flow holes 757a. As previously described, at the other end the HME 715 comprises preferably a tube 15a with connector 716a that can be coupled to the patient interface 716. A standard or an adjustable HME 715 could be used. An adjustable HME 715 is shown in the drawings, and can be configured to control the inlet airflow 54 and/or patient expiration airflow 755 over the HME material 756 to control the amount of humidity that is transferred. Any of the HMEs described herein could be used.

Apparatus Use

Use of the compact CPAP apparatus 1 will now be described with reference to FIG. 27. Due to its compact nature, the breathing apparatus 700 can be placed in a range of convenient locations, such as in the bed 770 next to a patient 771 being treated while they sleep. A convenient location means any location that: makes the breathing apparatus 700 easier to use or more comfortable to use, improves compliance and use of the apparatus, reduces the inconvenience to the user, reduces the disturbance to a user's sleep or in any other way assists the user to use the apparatus in better manner. This also enables the delivery tube 714 to be shorter, e.g. half the length, than used for traditional CPAP apparatus, which makes them thinner as well, resulting in a lighter and easier to manage tube.

The risk of placing the breathing apparatus 700 in a convenient location (as opposed to placing it in the usual manner on a clear bedside table or similar) is that the air inlet 714*a* might become occluded. The present invention reduces this risk by way of the flexible air inlet tube 713 that can be manipulated into a geometric configuration relative to the placement of the breathing apparatus so that the air inlet 713*a* is placed in a position that is not occluded, and is at low risk of being occluded due to movement of the patient 771 and/or that apparatus 700 throughout the night.

Figure 27:
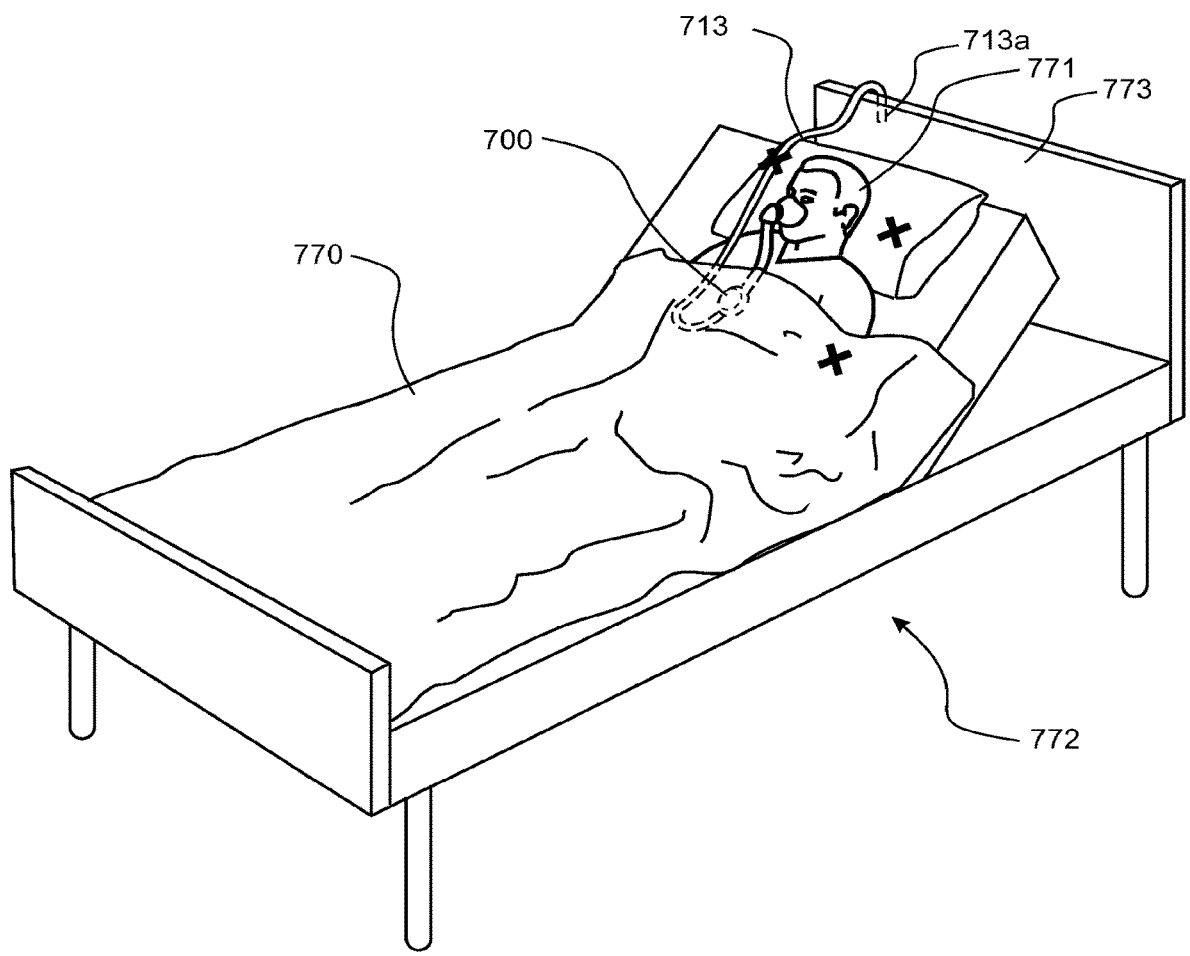
FIG. 27 shows an example of how a compact breathing apparatus could be used.

An example of use is shown in FIG. 27. In this case, the patient 771 has placed the breathing apparatus 700 next to them in bed 772 under the covers. Clearly, for a typical CPAP apparatus, this would not be possible due to its bulk, and also because the air inlet would be occluded by the covers. However, in this case the air inlet tube 713 is configured into a hook shape that can cook over the bed head 773 thus keeping the inlet 713*a* free from occlusion, and also restraining it against the bed head 773 so it is less likely to move. This is just one example and any suitable manipulation and geometric configuration of the air inlet tube 713 could be achieved. Other possibilities comprise having the CPAP apparatus hanging from the air inlet 713 on the bed head 773, or placed under the pillow, or placed next to the patient above the covers as shown by "X" in FIG. 27. Many alternatives are possible.

Additional Features

In an example, the flexible hose for the HME for coupling to the patient interface, has a 15 mm internal diameter (possibly anywhere between 10-20 mm) and/or is 50 to 100 mm long. These dimensions are exemplary only.

Preferably the breathing apparatus has no external configuration controls accessible for user manipulation. That is, no externally accessible controls for general operation, configuration or instruction of the apparatus (it might however have an external power switch, which would not be considered an external control in that case). The apparatus instead comprises a wireless user interface for wireless configuration and/or interrogation of the apparatus using a remote device, such as a smartphone, computer, remote control or the like. This would allow settings by a user and allow a user to view data and performance and for transfer to a server for viewing by third parties. The CPAP apparatus could activate (switch on and off) based on detecting patient breath, which would negate the need for a power switch. Alternatively, the apparatus has factory settings that are left as is, such as in an autotitration CPAP apparatus where operation can occur without external user adjustment.

In an example, the patient conduit is approximately 800 to 1000 mm long and/or 15 mm (or anywhere between 10-20 mm) internal diameter although these are exemplary dimensions only.

In an example, the housing is an extended oval shape with dimensions of 110×120×45 mm, but the dimensions can be anywhere between 80-120 mm×80-120 mm×40-60 mm (although these dimensions are exemplary dimensions only).

Preferably the flow generator housing halves are internally lined with a sound deadening material.

The present specification describes HMEs, both adjustable and non-adjustable, with various possible HME materials and material configurations. It also describes the incorporation (either integrated or retro fit) of any of the above HMEs in a patient interface. It also describes a compact CPAP apparatus with adjustable inlet. The embodiments described could be used in any combination.

The invention claimed is:

1. An apparatus comprising:
   a heat and moisture exchanger comprising a housing, the housing configured to removably connect to and disconnect from a first interface component, the first interface component comprising bias flow holes,
   the heat and moisture exchanger comprising an inlet into the housing, the inlet configured to couple to a source of gas, an outlet from the housing, the outlet configured to deliver gas to a patient, a gas flow path through the housing between the inlet and the outlet and through an HME material, and a slider, the HME material comprising a first side and a second side with HME bias flow holes on the first side and the second side, the slider being able to cover the HME bias flow holes on the first side and the second side and at least partially covering the HME bias flow holes on the first side at least partially opens the HME bias flow holes on the second side, the housing configured to enclose the HME material, the HME material being located within the housing in the gas flow path between the inlet and the outlet, and
   a ventilation cap not in contact with the gas flow path through the heat and moisture exchanger, the ventilation cap being configured to cover at least a portion of the bias flow holes of the first interface component, the heat and moisture exchanger being configured such that at least a portion of exhaled gases is forced through the heat and moisture exchanger instead of the bias flow holes when the ventilation cap covers at least a portion of the bias flow holes of the first interface component.

2. The apparatus according to claim 1, wherein the ventilation cap seals the bias flow holes of the first interface component when the heat and moisture exchanger is in use with the first interface component.

3. The apparatus according to claim 2, wherein the heat and moisture exchanger connects to the first interface component at the outlet of the heat and moisture exchanger.

4. The apparatus according to claim 1, wherein the heat and moisture exchanger connects to a second interface component or a conduit at the inlet of the heat and moisture exchanger.

5. The apparatus according to claim 1, wherein the first interface component further comprises a mask shell.

6. The apparatus according to claim 1, wherein the heat and moisture exchanger connects to a second interface component, wherein the second interface component comprises a mask frame.

7. The apparatus according to claim 1, wherein the first interface component further comprises an elbow.

8. The apparatus according to claim 1, wherein the ventilation cap comprises a first adjuster to open and/or close the bias flow holes of the first interface component.

9. The apparatus according to claim 1, wherein covering the HME bias flow holes on the first side of the HME material uncovers the HME bias flow holes on the second side of the HME material.

10. The apparatus according to claim 1, wherein the HME material is a metal or a polymer.

11. The apparatus according to claim 1, wherein the HME material is collided, layered and/or stacked to form air paths.

12. The apparatus according to claim 1, wherein the HME material comprises a sheet with raised portions.

13. The apparatus according to claim 1, wherein the HME material is located in a bi-directional portion of the gas flow path between the inlet and the outlet of the housing of the heat and moisture exchanger.

14. An apparatus comprising:
a patient interface, the patient interface comprising bias flow holes,
a heat and moisture exchanger comprising a housing, the housing configured to removably couple to the patient interface, the heat and moisture exchanger comprising an inlet into the housing, an outlet out of the housing, and a gas flow path defined through the housing between the inlet and the outlet, an HME material located within the housing and within the gas flow path between the inlet and the outlet, the housing configured to enclose the HME material, and a slider, the HME material comprising a first side and a second side with HME bias flow holes on the first side and the second side, the slider being able to cover the HME bias flow holes on the first side and the second side and at least partially covering the HME bias flow holes on the first side at least partially opens the HME bias flow holes on the second side, and
wherein the bias flow holes of the patient interface are configured to be sealed or adjusted when the heat and moisture exchanger is coupled to the patient interface, the heat and moisture exchanger being configured such that at least a portion of exhaled gases is forced through the heat and moisture exchanger instead of the bias flow holes of the patient interface when the bias flow holes of the patient interface are sealed or adjusted.

15. The apparatus according to claim 14, wherein the patient interface further comprises a patient contacting portion.

16. The apparatus according to claim 15 further comprising a ventilation cap configured to seal the bias flow holes of the patient interface.

17. The apparatus according to claim 15 further comprising a first adjuster to open and/or close the bias flow holes of the patient interface.

18. The apparatus according to claim 14, wherein the HME material is located in a bi-directional portion of the gas flow path between the inlet and the outlet of the housing of the heat and moisture exchanger.

19. An apparatus comprising:
a heat and moisture exchanger comprising a housing, the housing configured to removably connect to and disconnect from a first interface component; and
the heat and moisture exchanger comprising an inlet into the housing, the inlet configured to couple to a source of gas, an outlet from the housing, the outlet configured to deliver gas to a patient, a gas flow path through the housing between the inlet and the outlet and through an HME material, and a slider, the HME material comprising a first side and a second side with HME bias flow holes on the first side and the second side, the slider being able to cover the HME bias flow holes on the first side and the second side and at least partially covering the HME bias flow holes on the first side at least partially opens the HME bias flow holes on the second side, the housing configured to enclose the HME material, the HME material being located within the housing in the gas flow path between the inlet and the outlet.

* * * * *